US012349918B2

(12) United States Patent
Inouye

(10) Patent No.: US 12,349,918 B2
(45) Date of Patent: Jul. 8, 2025

(54) MULTI-SHARPNESS SPLIT TOP SOFT TISSUE ANCHORS

(71) Applicant: BOSTON SCIENTIFIC SCIMED, INC., Maple Grove, MN (US)

(72) Inventor: Joshua Mark Inouye, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 306 days.

(21) Appl. No.: 17/939,190

(22) Filed: Sep. 7, 2022

(65) Prior Publication Data

US 2023/0071725 A1 Mar. 9, 2023

Related U.S. Application Data

(60) Provisional application No. 63/241,608, filed on Sep. 8, 2021.

(51) Int. Cl.
*A61B 17/12* (2006.01)

(52) U.S. Cl.
CPC .. *A61B 17/12172* (2013.01); *A61B 17/12031* (2013.01); *A61B 17/12109* (2013.01)

(58) Field of Classification Search
CPC ........ A61B 17/12031; A61B 17/12109; A61B 17/12122; A61B 17/12172; A61B 17/12177; A61B 2017/00526
USPC ......................................................... 606/198
See application file for complete search history.

(56) References Cited

U.S. PATENT DOCUMENTS

| 178,283 A | 6/1876 | French |
| 1,967,318 A | 7/1934 | Monahan |
| 3,402,710 A | 9/1968 | Paleschuck |
| 3,540,431 A | 11/1970 | Mobin-Uddin |

(Continued)

FOREIGN PATENT DOCUMENTS

| CN | 1399571 A | 2/2003 |
| CN | 202143640 U | 2/2012 |

(Continued)

OTHER PUBLICATIONS

International Search Report and Written Opinion dated Aug. 3, 2004 for International Application No. PCT/US2004/008109.

(Continued)

*Primary Examiner* — Jocelin C Tanner
(74) *Attorney, Agent, or Firm* — Seager, Tufte & Wickhem LLP

(57) ABSTRACT

An occlusive implant may include an expandable framework configured to shift between a collapsed configuration and an expanded configuration, the expandable framework including a proximal end and a distal end. The expandable framework includes a plurality of anchor members extending radially outward from the expandable framework in the expanded configuration, each anchor member including a root portion fixedly attached to the expandable framework and extending distally to a trunk portion in the expanded configuration. At least a portion of the trunk portion extends radially outward relative to the root portion in the expanded configuration. At least one of the plurality of anchor members includes a plurality of branches extending radially outward from the trunk portion in the expanded configuration.

5 Claims, 19 Drawing Sheets

(56) References Cited

U.S. PATENT DOCUMENTS

| | | |
|---|---|---|
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,175,545 A | 11/1979 | Termanini |
| 4,309,776 A | 1/1982 | Berguer |
| 4,341,218 A | 7/1982 | Ü |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,133,733 A | 7/1992 | Rasmussen et al. |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,242,462 A | 9/1993 | El-Nounnou et al. |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |
| 5,776,097 A | 7/1998 | Massoud |
| 5,776,162 A | 7/1998 | Kleshinski |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |

(56) References Cited

U.S. PATENT DOCUMENTS

| | | |
|---|---|---|
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,902,289 A | 5/1999 | Swartz et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,931,818 A | 8/1999 | Werp et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,954,767 A | 9/1999 | Pajotin et al. |
| 5,957,940 A | 9/1999 | Tanner et al. |
| 5,961,545 A | 10/1999 | Entz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,159,195 A | 12/2000 | Ha et al. |
| 6,161,543 A | 12/2000 | Cox et al. |
| 6,168,615 B1 | 1/2001 | Ken et al. |
| 6,171,329 B1 | 1/2001 | Shaw et al. |
| 6,179,859 B1 | 1/2001 | Bates et al. |
| 6,193,739 B1 | 2/2001 | Chevillon et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,235,045 B1 | 5/2001 | Barbut et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,772 B1 | 7/2001 | Mulhauser et al. |
| 6,267,776 B1 | 7/2001 | O'Connell |
| 6,270,490 B1 | 8/2001 | Hahnen |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,319,251 B1 | 11/2001 | Tu et al. |
| 6,328,727 B1 | 12/2001 | Frazier et al. |
| 6,328,755 B1 | 12/2001 | Marshall |
| 6,342,062 B1 | 1/2002 | Suon et al. |
| 6,346,116 B1 | 2/2002 | Brooks et al. |
| 6,346,895 B1 | 2/2002 | Lee et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |
| 6,402,746 B1 | 6/2002 | Whayne et al. |
| 6,402,771 B1 | 6/2002 | Palmer et al. |
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,454,775 B1 | 9/2002 | Demarais et al. |
| 6,458,145 B1 | 10/2002 | Ravenscroft et al. |
| 6,464,712 B1 | 10/2002 | Epstein et al. |
| 6,468,291 B2 | 10/2002 | Bates et al. |
| 6,468,301 B1 | 10/2002 | Amplatz et al. |
| 6,485,501 B1 | 11/2002 | Green |
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,533,782 B2 | 3/2003 | Howell et al. |

(56) References Cited

U.S. PATENT DOCUMENTS

| | | |
|---|---|---|
| 6,547,760 B1 | 4/2003 | Samson et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,569,184 B2 | 5/2003 | Huter |
| 6,569,214 B2 | 5/2003 | Williams et al. |
| 6,589,214 B2 | 7/2003 | McGuckin et al. |
| 6,589,251 B2 | 7/2003 | Yee et al. |
| 6,599,308 B2 | 7/2003 | Amplatz |
| 6,602,271 B2 | 8/2003 | Adams et al. |
| 6,623,508 B2 | 9/2003 | Shaw et al. |
| 6,641,564 B1 | 11/2003 | Kraus |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,712,836 B1 | 3/2004 | Berg et al. |
| 6,726,701 B2 | 4/2004 | Gilson et al. |
| 6,730,108 B2 | 5/2004 | Van Tassel et al. |
| 6,755,812 B2 | 6/2004 | Peterson et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,942,653 B2 | 9/2005 | Quinn |
| 6,949,113 B2 | 9/2005 | Van Tassel et al. |
| 6,958,061 B2 | 10/2005 | Truckai et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,128,073 B1 | 10/2006 | van der Burg et al. |
| 7,152,605 B2 | 12/2006 | Khairkhahan et al. |
| 7,169,164 B2 | 1/2007 | Borillo et al. |
| 7,179,275 B2 | 2/2007 | McGuckin, Jr. et al. |
| 7,226,466 B2 | 6/2007 | Opolski |
| 7,303,526 B2 | 12/2007 | Sharkey et al. |
| 7,323,002 B2 | 1/2008 | Johnson et al. |
| 7,597,704 B2 | 10/2009 | Frazier et al. |
| 7,678,123 B2 | 3/2010 | Chanduszko |
| 7,695,425 B2 | 4/2010 | Schweich et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,780,694 B2 | 8/2010 | Palmer et al. |
| 7,794,472 B2 | 9/2010 | Eidenschink et al. |
| 7,799,049 B2 | 9/2010 | Ostrovsky et al. |
| 7,803,171 B1 | 9/2010 | Uflacker |
| 7,811,300 B2 | 10/2010 | Feller, III et al. |
| 7,811,314 B2 | 10/2010 | Fierens et al. |
| 7,862,500 B2 | 1/2011 | Khairkhahan et al. |
| 7,927,365 B2 | 4/2011 | Fierens et al. |
| 7,959,645 B2 | 6/2011 | WasDyke et al. |
| 7,972,359 B2 | 7/2011 | Kreidler |
| 8,025,495 B2 | 9/2011 | Hardert et al. |
| 8,043,329 B2 | 10/2011 | Khairkhahan et al. |
| 8,052,715 B2 | 11/2011 | Quinn et al. |
| 8,062,282 B2 | 11/2011 | Kolb |
| 8,080,032 B2 | 12/2011 | van der Burg et al. |
| 8,097,015 B2 | 1/2012 | Devellian |
| 8,221,384 B2 | 7/2012 | Frazier et al. |
| 8,221,445 B2 | 7/2012 | van Tassel et al. |
| 8,246,648 B2 | 8/2012 | Tekulve |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,491,623 B2 | 7/2013 | Vogel et al. |
| 8,523,897 B2 | 9/2013 | van der Burg et al. |
| 8,535,343 B2 | 9/2013 | van der Burg et al. |
| 8,562,509 B2 | 10/2013 | Bates |
| 8,663,273 B2 | 3/2014 | Khairkhahan et al. |
| 8,685,055 B2 | 4/2014 | VanTassel et al. |
| 8,740,931 B2 | 6/2014 | Snow |
| 8,834,519 B2 | 9/2014 | van der Burg et al. |
| 8,845,711 B2 | 9/2014 | Miles et al. |
| 8,998,944 B2 | 4/2015 | Thornton |
| 9,034,006 B2 | 5/2015 | Quinn et al. |
| 9,132,000 B2 | 9/2015 | VanTassel et al. |
| 9,168,043 B2 | 10/2015 | van der Burg et al. |
| 9,186,152 B2 | 11/2015 | Campbell et al. |
| 9,211,124 B2 | 12/2015 | Campbell et al. |
| 9,445,895 B2 | 9/2016 | Kreidler |
| 9,554,806 B2 | 1/2017 | Larsen et al. |
| 9,561,037 B2 | 2/2017 | Fogarty et al. |
| 9,561,097 B1 | 2/2017 | Kim et al. |
| 9,629,636 B2 | 4/2017 | Fogarty et al. |
| 9,700,323 B2 | 6/2017 | Clark |
| 9,730,701 B2 | 8/2017 | Tischler et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,071,181 B1 | 9/2018 | Penegor et al. |
| 10,076,335 B2 | 9/2018 | Zaver et al. |
| 10,111,645 B2 | 10/2018 | Fearnot et al. |
| 10,143,458 B2 | 12/2018 | Kreidler |
| 10,258,454 B2 | 4/2019 | Molgaard-Nielsen et al. |
| 10,603,020 B2 | 3/2020 | Rudman et al. |
| 10,939,986 B2 | 3/2021 | Chen et al. |
| 11,039,822 B2 | 6/2021 | Wang et al. |
| 2001/0000797 A1 | 5/2001 | Mazzocchi |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082638 A1 | 6/2002 | Porter et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |
| 2003/0017775 A1 | 1/2003 | Dong et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0181942 A1* | 9/2003 | Sutton ............. A61B 17/0057 606/200 |
| 2003/0191526 A1 | 10/2003 | Van Tassel et al. |
| 2003/0195555 A1 | 10/2003 | Khairkhahan et al. |
| 2003/0204203 A1 | 10/2003 | Khairkhahan et al. |
| 2003/0208214 A1 | 11/2003 | Loshakove et al. |
| 2003/0220667 A1 | 11/2003 | van der Burg et al. |
| 2004/0034366 A1 | 2/2004 | van der Burg et al. |
| 2004/0049210 A1 | 3/2004 | VanTassel et al. |
| 2004/0093012 A1 | 5/2004 | Cully et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0158274 A1 | 8/2004 | WasDyke |
| 2004/0186486 A1 | 9/2004 | Roue et al. |
| 2004/0215230 A1 | 10/2004 | Frazier et al. |
| 2004/0220610 A1 | 11/2004 | Kreidler et al. |
| 2004/0220682 A1 | 11/2004 | Levine et al. |
| 2004/0230222 A1 | 11/2004 | van der Burg et al. |
| 2005/0004652 A1 | 1/2005 | van der Burg et al. |

(56) References Cited

U.S. PATENT DOCUMENTS

| | | |
|---|---|---|
| 2005/0015109 A1 | 1/2005 | Lichtenstein |
| 2005/0038470 A1 | 2/2005 | van der Burg et al. |
| 2005/0049573 A1 | 3/2005 | Van Tassel et al. |
| 2005/0070952 A1 | 3/2005 | Devellian |
| 2005/0113861 A1 | 5/2005 | Corcoran et al. |
| 2005/0125020 A1 | 6/2005 | Meade et al. |
| 2005/0177182 A1 | 8/2005 | van der Burg et al. |
| 2005/0203568 A1 | 9/2005 | Burg et al. |
| 2005/0283186 A1 | 12/2005 | Berrada et al. |
| 2005/0288704 A1 | 12/2005 | Cartier et al. |
| 2006/0015136 A1 | 1/2006 | Besselink |
| 2006/0030877 A1 | 2/2006 | Martinez et al. |
| 2006/0052816 A1 | 3/2006 | Bates et al. |
| 2006/0100658 A1 | 5/2006 | Obana et al. |
| 2006/0155323 A1 | 7/2006 | Porter et al. |
| 2007/0066993 A1* | 3/2007 | Kreidler ............ A61B 17/12122 606/213 |
| 2007/0083227 A1 | 4/2007 | van der Burg et al. |
| 2007/0083230 A1 | 4/2007 | Javois |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0256669 A1 | 10/2010 | Harris et al. |
| 2010/0324585 A1 | 12/2010 | Miles et al. |
| 2011/0054515 A1 | 3/2011 | Bridgeman et al. |
| 2011/0082495 A1 | 4/2011 | Ruiz |
| 2011/0098525 A1 | 4/2011 | Kermode et al. |
| 2011/0218566 A1 | 9/2011 | van der Burg et al. |
| 2011/0301630 A1 | 12/2011 | Hendriksen et al. |
| 2012/0029553 A1 | 2/2012 | Quinn et al. |
| 2012/0035643 A1 | 2/2012 | Khairkhahan et al. |
| 2012/0065662 A1 | 3/2012 | van der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0283585 A1 | 11/2012 | Werneth et al. |
| 2012/0283773 A1 | 11/2012 | Van Tassel et al. |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0110154 A1 | 5/2013 | van der Burg et al. |
| 2013/0165735 A1 | 6/2013 | Khairkhahan et al. |
| 2013/0178889 A1 | 7/2013 | Miles et al. |
| 2013/0211492 A1 | 8/2013 | Schneider et al. |
| 2013/0331884 A1 | 12/2013 | Van der Burg et al. |
| 2014/0018841 A1 | 1/2014 | Peiffer et al. |
| 2014/0039536 A1 | 2/2014 | Cully et al. |
| 2014/0046360 A1 | 2/2014 | van der Burg et al. |
| 2014/0081314 A1 | 3/2014 | Zaver et al. |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0303719 A1 | 10/2014 | Cox et al. |
| 2014/0336612 A1 | 11/2014 | Frydlewski et al. |
| 2014/0336699 A1 | 11/2014 | van der Burg et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van der Burg et al. |
| 2016/0192942 A1 | 7/2016 | Strauss et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0100112 A1 | 4/2017 | van der Burg et al. |
| 2017/0119400 A1 | 5/2017 | Amplatz et al. |
| 2017/0181751 A1 | 6/2017 | Larsen et al. |
| 2017/0340336 A1 | 11/2017 | Osypka |
| 2018/0064446 A1 | 3/2018 | Figulla et al. |
| 2018/0070950 A1 | 3/2018 | Zaver et al. |
| 2018/0140412 A1 | 5/2018 | Sutton et al. |
| 2018/0140413 A1 | 5/2018 | Quinn et al. |
| 2018/0250014 A1 | 9/2018 | Melanson et al. |
| 2018/0310925 A1* | 11/2018 | Inouye ............. A61B 17/12031 |
| 2019/0046213 A1 | 2/2019 | Gong et al. |
| 2019/0083224 A1 | 3/2019 | Tessmer |
| 2019/0117367 A1 | 4/2019 | Simpson |
| 2019/0125362 A1 | 5/2019 | Tischler |
| 2019/0167242 A1 | 6/2019 | Rowe et al. |
| 2019/0223883 A1 | 7/2019 | Anderson et al. |
| 2019/0298380 A1 | 10/2019 | Inouye et al. |
| 2019/0299011 A1 | 10/2019 | Chu |
| 2020/0008812 A1 | 1/2020 | Inouye et al. |
| 2020/0060801 A1 | 2/2020 | Yang |
| 2020/0060849 A1 | 2/2020 | Inouye et al. |
| 2020/0178981 A1 | 6/2020 | Anderson et al. |
| 2021/0015596 A1 | 1/2021 | Nigon |

FOREIGN PATENT DOCUMENTS

| | | |
|---|---|---|
| CN | 106859722 A | 6/2017 |
| DE | 10201004476 A1 | 3/2012 |
| EP | 1523957 A2 | 4/2005 |
| EP | 1595504 A1 | 11/2005 |
| EP | 2074953 A1 | 1/2009 |
| EP | 2481381 A1 | 8/2012 |
| EP | 2928420 A1 | 10/2015 |
| EP | 3072461 A1 | 9/2016 |
| EP | 3372173 A2 | 9/2018 |
| JP | 2003532457 A | 11/2003 |
| JP | 2005324019 A | 11/2005 |
| JP | 2007513684 A | 5/2007 |
| JP | 2009160402 A | 7/2009 |
| JP | 2012501793 A | 1/2012 |
| WO | 9313712 A1 | 7/1993 |
| WO | 9504132 A1 | 2/1995 |
| WO | 9522359 A1 | 8/1995 |
| WO | 9601591 A1 | 1/1996 |
| WO | 9640356 A1 | 12/1996 |
| WO | 9721402 A1 | 6/1997 |
| WO | 9726939 A1 | 7/1997 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9822026 A1 | 5/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |

(56) References Cited

FOREIGN PATENT DOCUMENTS

| | | | |
|---|---|---|---|
| WO | 9930640 A1 | 6/1999 |
| WO | 9944510 A1 | 9/1999 |
| WO | 9959479 A1 | 11/1999 |
| WO | 0001308 A1 | 1/2000 |
| WO | 0016705 A1 | 3/2000 |
| WO | 0027292 A1 | 5/2000 |
| WO | 0035352 A1 | 6/2000 |
| WO | 0053120 A1 | 9/2000 |
| WO | 0067669 A1 | 11/2000 |
| WO | 0108743 A1 | 2/2001 |
| WO | 0115629 A1 | 3/2001 |
| WO | 0121247 A1 | 3/2001 |
| WO | 0126726 A1 | 4/2001 |
| WO | 0130266 A1 | 5/2001 |
| WO | 0130267 A1 | 5/2001 |
| WO | 0130268 A1 | 5/2001 |
| WO | 0170119 A1 | 9/2001 |
| WO | 0215793 A2 | 2/2002 |
| WO | 0224106 A2 | 3/2002 |
| WO | 02071977 A2 | 9/2002 |
| WO | 03007825 A1 | 1/2003 |
| WO | 03008030 A2 | 1/2003 |
| WO | 03032818 A1 | 4/2003 |
| WO | 2004012629 A1 | 2/2004 |
| WO | 2007044536 A1 | 4/2007 |
| WO | 2010024801 A1 | 3/2010 |
| WO | 2010081033 A1 | 7/2010 |
| WO | 2013060855 A1 | 5/2013 |
| WO | 2013159065 A1 | 10/2013 |
| WO | 2014011865 A1 | 1/2014 |
| WO | 2014018907 A1 | 1/2014 |
| WO | 2014089129 A1 | 6/2014 |
| WO | 201406239 A1 | 7/2014 |
| WO | 2015164836 A1 | 10/2015 |
| WO | 2016087145 A1 | 6/2016 |
| WO | 2018017935 A1 | 1/2018 |
| WO | 2018187732 A1 | 10/2018 |
| WO | 2019084358 A1 | 5/2019 |

OTHER PUBLICATIONS

International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al, "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.
Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Tung et al., U.S. Appl. No. 61/559,941, filed Nov. 15, 2011.
Yue Yu et al., U.S. Appl. No. 61/557,880, filed Dec. 20, 2011.
Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
Invitation to Pay Additional Fees and, Where Applicable, Protest Fee, mailed Oct. 13, 2016.
International Search Report and Written Opinion dated Oct. 14, 2019 for International Application No. PCT/US2019/047452.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 20, for International Application No. PCT/US2019/065243.
International Search Report and Written Opinion dated Sep. 9, 2019 for International Application No. PCT/US2019/033698.
Blackshear et al; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation to Pay Additional Fees dated Feb. 22, 2019 for International Application No. PCT/US2018/066163.
International Search Report and Written Opinion dated Oct. 23, 2020 for International Application No. PCT/US2020/042192.
International Search Report and Written Opinion dated Dec. 6, 2022 for International Application No. PCT/US2022/042696.

\* cited by examiner

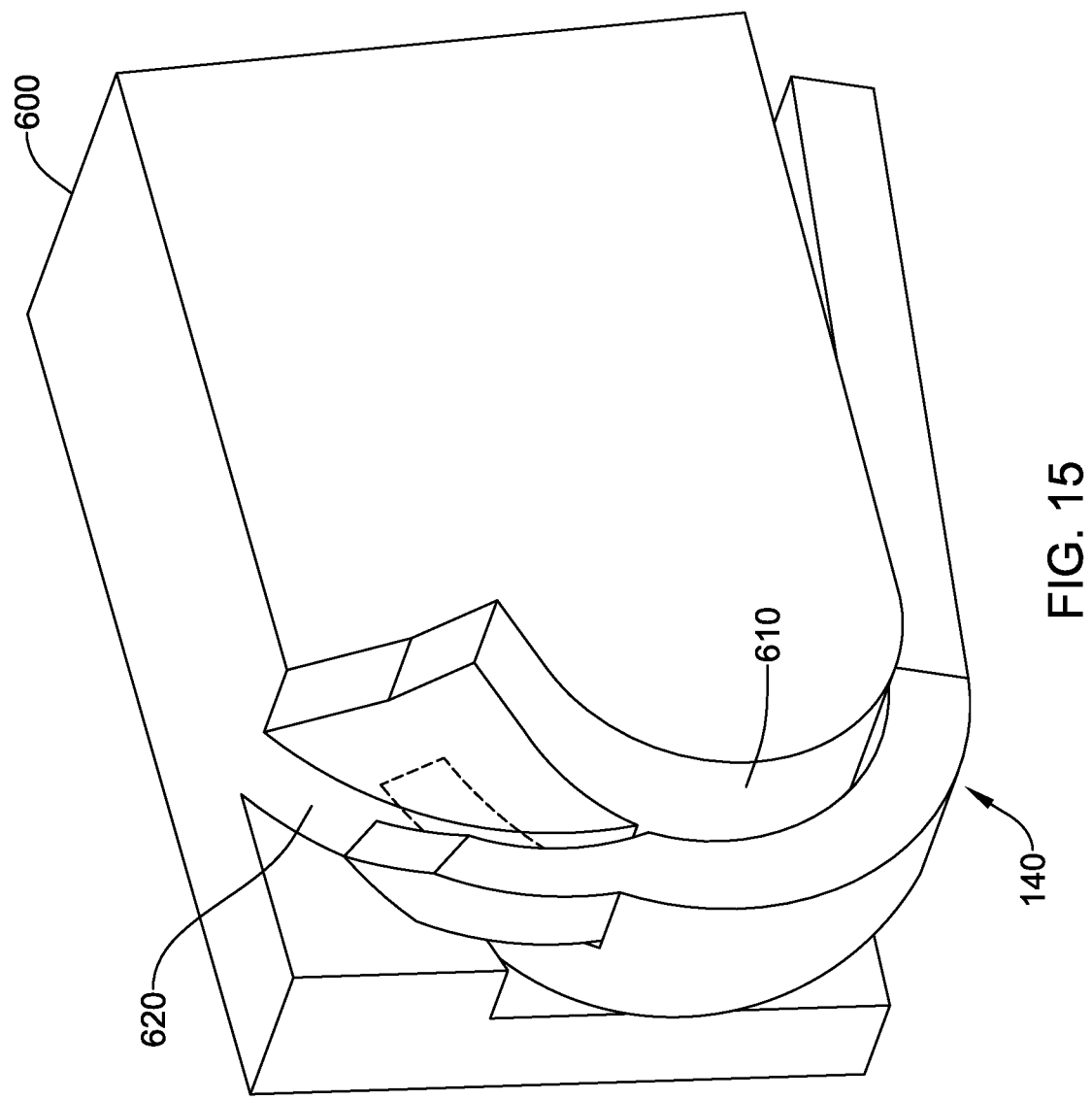

MULTI-SHARPNESS SPLIT TOP SOFT TISSUE ANCHORS

CROSS-REFERENCE TO RELATED APPLICATIONS

This application claims the benefit of priority of U.S. Provisional Application No. 63/241,608 filed Sep. 8, 2021, the entire disclosure of which is hereby incorporated by reference.

TECHNICAL FIELD

The disclosure relates generally to medical devices and more particularly to occlusive implants adapted for use in percutaneous medical procedures including implantation into the left atrial appendage (LAA) of a heart.

BACKGROUND

The left atrial appendage is a small organ attached to the left atrium of the heart. During normal heart function, as the left atrium constricts and forces blood into the left ventricle, the left atrial appendage constricts and forces blood into the left atrium. The ability of the left atrial appendage to contract assists with improved filling of the left ventricle, thereby playing a role in maintaining cardiac output. However, in patients suffering from atrial fibrillation, the left atrial appendage may not properly contract or empty, causing stagnant blood to pool within its interior, which can lead to the undesirable formation of thrombi within the left atrial appendage.

Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation originate in the left atrial appendage. As a treatment, medical devices have been developed which are deployed to close off the left atrial appendage. Of the known medical devices and methods, each has certain advantages and disadvantages. There is an ongoing need to provide alternative medical devices as well as alternative methods for manufacturing and using medical devices.

SUMMARY

In one example, an occlusive implant may comprise an expandable framework configured to shift between a collapsed configuration and an expanded configuration, the expandable framework including a proximal end and a distal end. The expandable framework may include a plurality of anchor members extending radially outward from the expandable framework in the expanded configuration, each anchor member including a root portion fixedly attached to the expandable framework and extending distally to a trunk portion in the expanded configuration. At least a portion of the trunk portion may extend radially outward relative to the root portion in the expanded configuration. At least one of the plurality of anchor members may include a plurality of branches extending radially outward from the trunk portion in the expanded configuration.

In addition or alternatively to any example described herein, a tip portion of each branch of the plurality of branches extends proximally from a distalmost portion of its respective branch.

In addition or alternatively to any example described herein, the plurality of branches includes a first branch and a second branch.

In addition or alternatively to any example described herein, the first branch includes a rounded tip and the second branch includes a sharpened tip.

In addition or alternatively to any example described herein, the first branch extends proximally more than the second branch.

In addition or alternatively to any example described herein, the second branch extends radially outward a greater distance from a central longitudinal axis of the expandable framework than the first branch.

In addition or alternatively to any example described herein, the first branch includes a proximally facing first curved surface defined by a first radius and a first center and the second branch includes a proximally facing second curved surface defined by a second radius and a second center, wherein the second center is offset radially outward from the first center relative to a central longitudinal axis of the expandable framework.

In addition or alternatively to any example described herein, the plurality of branches further includes a third branch.

In addition or alternatively to any example described herein, at least one of the first branch, second branch, and third branch includes a rounded tip.

In addition or alternatively to any example described herein, each branch of the plurality of branches is configured to penetrate tissue.

In addition or alternatively to any example described herein, each branch of the plurality of branches is curved.

In addition or alternatively to any example described herein, each branch of the plurality of branches is curved in a radially outward direction from the trunk portion.

In addition or alternatively to any example described herein, each branch of the plurality of branches is curved in a proximal direction from the trunk portion.

In addition or alternatively to any example described herein, at least one branch of the plurality of branches has a concave cross-section facing toward the proximal end of the expandable framework.

In addition or alternatively to any example described herein, an occlusive implant system may comprise a sheath including an implant containment area proximate a distal end of the sheath; and an occlusive implant comprising an expandable framework configured to shift between a collapsed configuration and an expanded configuration, the expandable framework including a proximal end and a distal end. The expandable framework may include a plurality of anchor members extending radially outward from the expandable framework in the expanded configuration, each anchor member including a root portion fixedly attached to the expandable framework and extending distally to a trunk portion in the expanded configuration. At least a portion of the trunk portion may extend radially outward relative to the root portion in the expanded configuration. At least one of the plurality of anchor members may include a plurality of branches extending radially outward from the trunk portion in the expanded configuration. Recapturing the occlusive implant within the implant containment area after shifting to the expanded configuration may include advancing the distal end of the sheath distally into contact with the plurality of anchor members, wherein contact between the distal end of the sheath and at least one of the plurality of branches urges remaining branches of the plurality of branches away from contact with the sheath.

In addition or alternatively to any example described herein, each branch contacted by the distal end of the sheath includes a rounded tip and each remaining branch includes a sharpened tip.

In addition or alternatively to any example described herein, each sharpened tip is disposed distal of each rounded tip as measured parallel to a central longitudinal axis of the expandable framework.

In addition or alternatively to any example described herein, distal advancement of the sheath after contact between the distal end of the sheath and at least one of the plurality of branches deflects the at least one of the plurality of anchor members at the trunk portion.

In addition or alternatively to any example described herein, each branch of the plurality of branches has a concave cross-section facing toward the proximal end of the expandable framework in the expanded configuration.

In addition or alternatively to any example described herein, an occlusive implant system may comprise an expandable framework configured to shift between a collapsed configuration and an expanded configuration, the expandable framework including a proximal end and a distal end. The expandable framework may include a plurality of anchor members extending radially outward from the expandable framework in the expanded configuration, each anchor member including a root portion fixedly attached to the expandable framework and extending distally to a trunk portion in the expanded configuration. At least a portion of the trunk portion may curve radially outward relative to the root portion in the expanded configuration and is defined by a center. At least one of the plurality of anchor members may include a plurality of branches extending radially outward from the trunk portion in the expanded configuration. The plurality of branches may include a first branch having a first curve defined by first center in the expanded configuration and a second branch having a second curve defined by a second center in the expanded configuration. The first center and the center of the at least a portion of the trunk portion may be disposed a first radial distance from a central longitudinal axis of the expandable framework in the expanded configuration, and the second center may be disposed a second radial distance from the central longitudinal axis greater than the first radial distance in the expanded configuration.

The above summary of some embodiments, aspects, and/or examples is not intended to describe each embodiment or every implementation of the present disclosure. The figures and the detailed description more particularly exemplify aspects of these embodiments.

BRIEF DESCRIPTION OF THE DRAWINGS

The disclosure may be more completely understood in consideration of the following detailed description in connection with the accompanying drawings, in which:

FIG. 15 illustrates selected aspects of an alternative configuration of shape set tooling associated with the occlusive implant.

Figure 1:
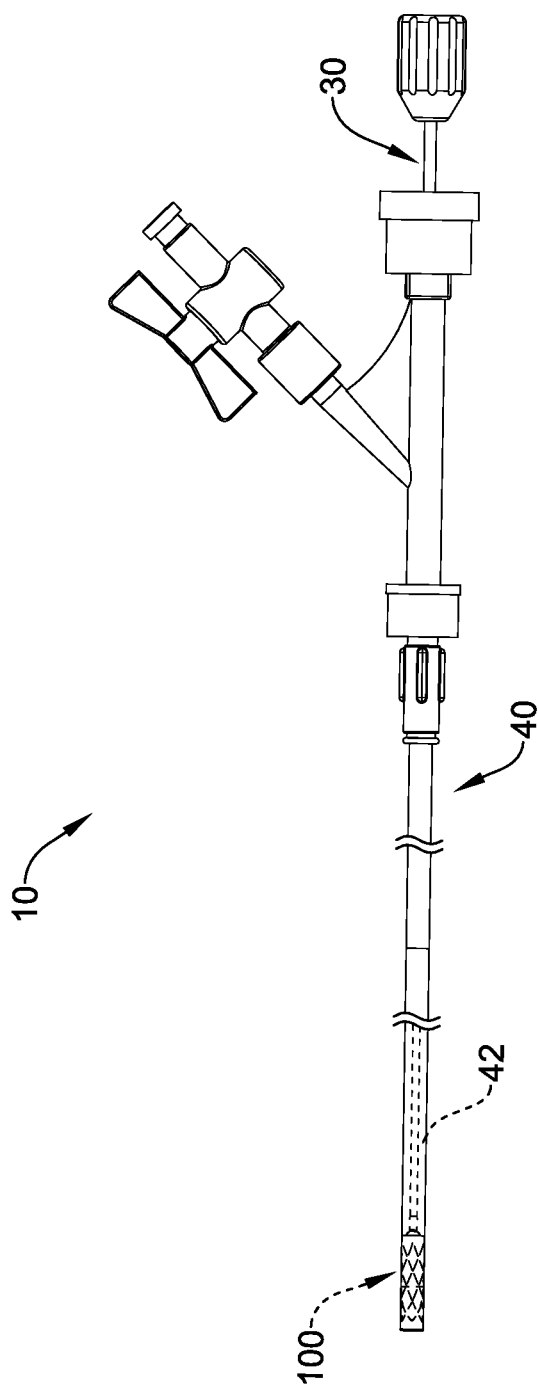
FIGS. 1-2 are side views of an occlusive implant system.

While aspects of the disclosure are amenable to various modifications and alternative forms, examples are shown in the drawings and described herein. It should be understood, however, that the intention is not to limit aspects of the disclosure to the particular embodiments described. On the contrary, the disclosure shall cover all modifications, equivalents, and alternatives falling within the spirit and scope thereof.

DETAILED DESCRIPTION

The following description should be read with reference to the drawings, which are not necessarily to scale, wherein like reference numerals indicate like elements throughout the several views. The detailed description and drawings are intended to illustrate but not limit the present disclosure. Those skilled in the art will recognize that the various elements described and/or shown may be arranged in various combinations and configurations without departing from the scope of the disclosure. The detailed description and drawings illustrate exemplary aspects of the disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, all elements of the present disclosure are not necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The left atrial appendage may be attached to and in fluid communication with a left atrium of a patient's heart. In some patients, the left atrial appendage may have a complex geometry and/or irregular surface area. Those of skill in the art will also recognize that the medical devices and methods disclosed herein may be adapted for various sizes and shapes of the left atrial appendage, as necessary. The left atrial appendage may include a generally longitudinal axis arranged along a depth of a main body of the left atrial appendage. The main body may include a wall and an ostium forming a proximal mouth. In some embodiments, a lateral extent of the ostium and/or the wall may be smaller or less than a depth of the main body along the longitudinal axis, or a depth of the main body may be greater than a lateral extent of the ostium and/or the wall. In some embodiments, the left atrial appendage may include a tail-like element associated with a distal portion of the main body, which element may protrude radially or laterally away from the main body.

The following figures illustrate selected components and/or arrangements of a left atrial appendage closure device, a left atrial appendage closure device system, and/or methods of using the left atrial appendage closure device and/or the left atrial appendage closure device system. It should be noted that in any given figure, some features may not be shown, or may be shown schematically, for simplicity. Additional details regarding some of the components of the implant and/or the system may be illustrated in other figures in greater detail. While discussed in the context of occluding the left atrial appendage, the left atrial appendage closure device and/or the left atrial appendage closure device system may also be used for other interventions and/or percutaneous medical procedures within a patient. Similarly, the devices and methods described herein with respect to percutaneous deployment may be used in other types of surgical procedures, as appropriate. For example, in some examples, the devices may be used in a non-percutaneous procedure. Devices and methods in accordance with the disclosure may also be adapted and configured for other uses within the anatomy.

Figure 2:
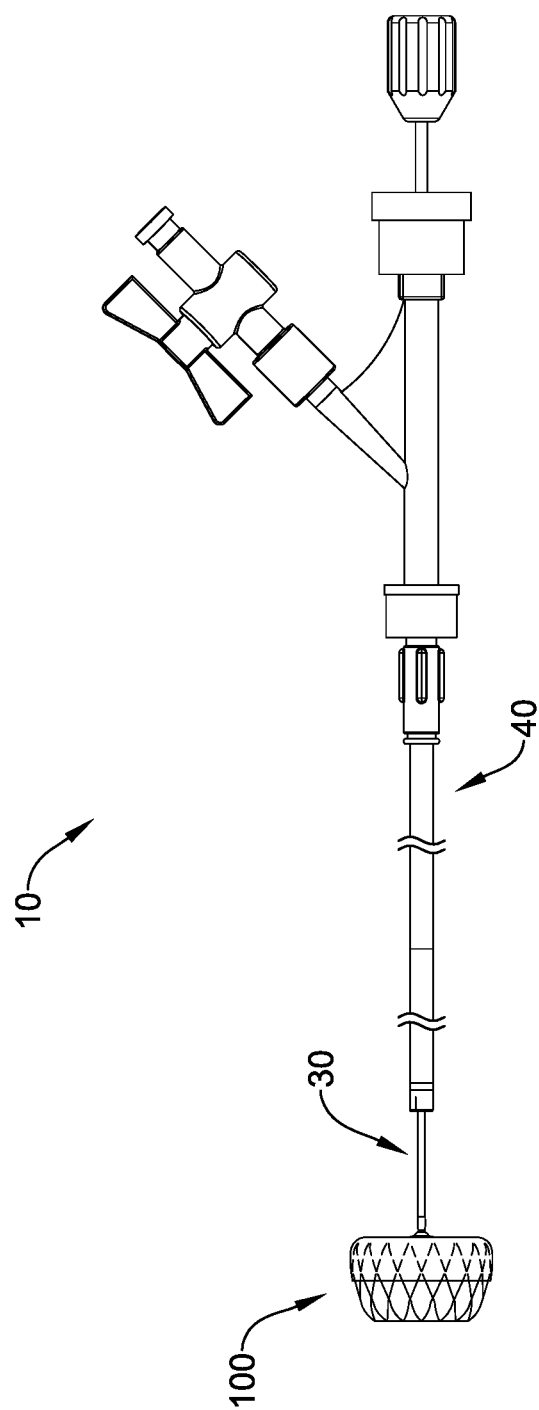

The figures illustrate selected components and/or arrangements of an occlusive implant system 10, shown schematically in FIGS. 1-2 for example. It should be noted that in any given figure, some features of the occlusive implant system 10 may not be shown, or may be shown schematically, for simplicity. Additional details regarding some of the components of the occlusive implant system 10 may be illustrated in other figures in greater detail. In some embodiments, the occlusive implant system 10 may include a delivery device that can be used for percutaneous delivery of an occlusive implant to an area of interest in the anatomy, such as a left atrial appendage. In some embodiments, the occlusive implant system 10 may include a delivery device that can be used for percutaneous delivery of a replacement heart valve implant (e.g., a replacement mitral valve, a replacement aortic valve, etc.) to an area of interest in the anatomy, such as a native heart valve. This, however, is not intended to be limiting as the occlusive implant system 10 and/or the delivery device may also be used for other interventions including valve repair, valvuloplasty, and the like, or other similar interventions.

The occlusive implant system 10 may include a sheath 40 having a lumen 42 extending from a proximal opening to a distal opening, a core wire 30 slidably disposed within the lumen 42, and an occlusive implant 100 having an expandable framework 110 configure to shift between a collapsed configuration (e.g., FIG. 1), wherein the occlusive implant 100 is disposed within an implant containment area of the sheath 40 proximate a distal end of the sheath 40 and/or the distal opening in the collapsed configuration, and an expanded configuration (e.g., FIG. 2), wherein the occlusive implant 100 and/or the expandable framework 110 is configured to shift between the collapsed configuration and the expanded configuration when the occlusive implant 100 is disposed distal of the distal end of the sheath 40 and/or the distal opening, and/or when the occlusive implant 100 is distal of and/or outside of the implant containment area of the sheath 40. The occlusive implant 100 may be disposed at and/or releasably connected to a distal portion of the core wire 30. The core wire 30 may be slidably and/or rotatably disposed within the lumen 42 of the sheath 40 and/or the implant containment area of the sheath 40. In some embodiments, a proximal end of the core wire 30 may extend proximally of a proximal end of the sheath 40 and/or the proximal opening of the lumen 42 for manual manipulation by a clinician or practitioner. In some embodiments, the example occlusive implant 100 may be removably attached, joined, or otherwise connected to the distal end of the core wire 30. The core wire 30 may be configured to and/or may be capable of axially translating the occlusive implant 100 relative to the sheath 40 and/or the implant containment area of the sheath 40. In one example, the core wire 30 may be advanced distally while the sheath 40 is held in a constant position. In another example, the core wire 30 may be advanced distally while the sheath 40 is retracted proximally. In yet another example, the core wire 30 may be held in a constant position while the sheath 40 is retracted proximally relative to the core wire 30 and/or the occlusive implant 100. Other configurations are also contemplated. The sheath 40 and/or the core wire 30 may have a selected level of axial stiffness and/or pushability characteristics while also having a selected level of flexibility to permit navigation through the patient's vasculature.

Some suitable, but non-limiting, examples of materials for the occlusive implant system 10, the core wire 30, the sheath 40, and/or the occlusive implant 100, etc. are discussed below. It is contemplated that any exemplary occlusive implant and/or feature thereof disclosed herein may be used in accordance with and/or be associated with the example occlusive implant system 10 described above.

Figure 3:
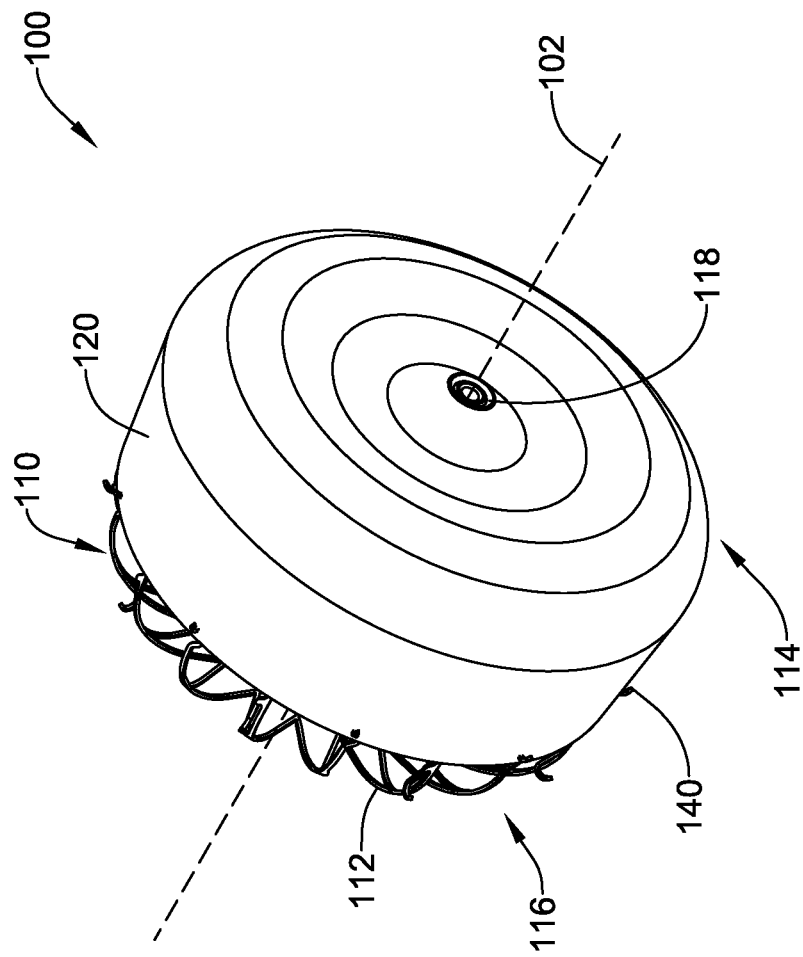
FIGS. 3-4 illustrate selected aspects of an occlusive implant.
Figure 4:
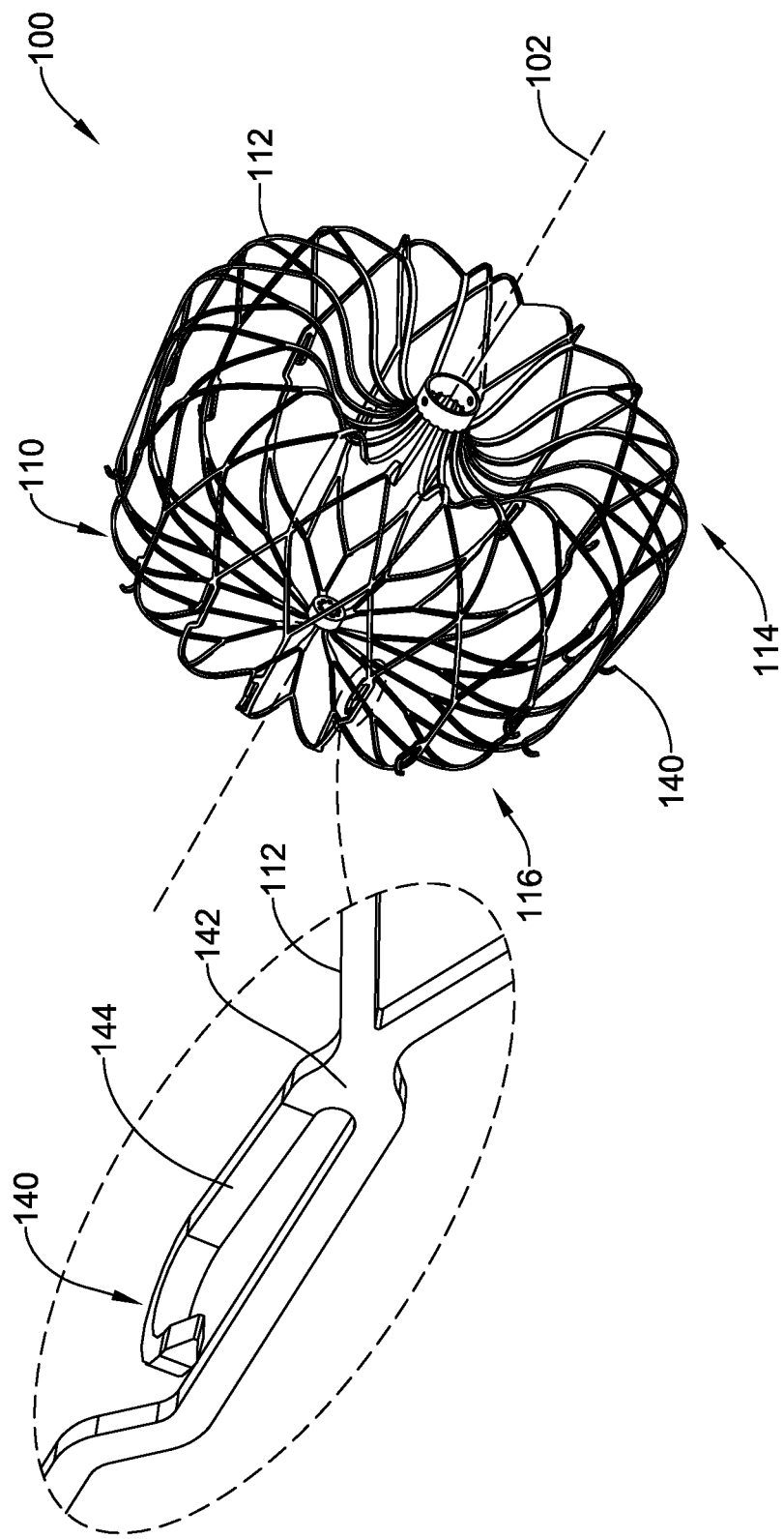

FIGS. 3-4 illustrate an example configuration of the occlusive implant 100 comprising the expandable framework 110 configured to shift axially and/or radially along a central longitudinal axis 102 between the collapsed configuration and the expanded configuration. The expandable framework 110 may comprise a plurality of interconnected struts 112 defining a plurality of cells. In some embodiments, the plurality of cells may be a plurality of closed cells. In some embodiments, the plurality of cells may be a plurality of open cells. In some embodiments, the plurality of cells may include a plurality of open cells and a plurality of closed cells in various combinations and/or arrangements. The expandable framework 110 may be compliant and substantially conform to and/or be in sealing engagement with the shape and/or geometry of an ostium and/or a lateral wall of a left atrial appendage in the expanded configuration. In some embodiments, the occlusive implant 100 may expand to a size, extent, or shape less than or different from a maximum unconstrained extent, as determined by the surrounding tissue, the ostium, and/or the lateral wall of the left atrial appendage. In some embodiments, reducing a thickness of various elements of the expandable framework 110 may increase the flexibility and compliance of the expandable framework 110 and/or the occlusive implant 100, thereby permitting the expandable framework 110 and/or the occlusive implant 100 to conform to the tissue around it, rather than forcing the tissue to conform to the expandable framework 110 and/or the occlusive implant 100.

The expandable framework 110 may include a proximal end 114 and a distal end 116. In some embodiments, the expandable framework 110 may include a proximal hub 118 configured to releasably attach, join, couple, engage, or otherwise connect to a distal end of the core wire 30. In some embodiments, the proximal hub 118 of the expandable framework 110 may include a threaded insert coupled thereto. In some embodiments, the threaded insert may be configured to and/or adapted to couple with, join to, mate with, or otherwise engage a threaded member disposed at the distal end of the core wire 30. In some embodiments, the proximal hub 118 may include internal threads configured to rotatably and/or threadably engage an externally threaded distal end of the core wire 30. Other means of releasably coupling and/or engaging the proximal hub 118 of the expandable framework 110 to the distal end of the core wire 30 are also contemplated. As noted herein, some features are not shown in every figure to improve clarity.

The expandable framework 110 and/or the plurality of interconnected struts 112 may be formed and/or cut from a tubular member. In some embodiments, the expandable framework 110 and/or the plurality of interconnected struts 112 may be integrally formed and/or cut from a unitary member. In some embodiments, the expandable framework 110 and/or the plurality of interconnected struts 112 may be integrally formed and/or cut from a unitary tubular member and subsequently formed and/or heat set to a desired shape in the expanded configuration. In some embodiments, the expandable framework 110 and/or the plurality of interconnected struts 112 may be integrally formed and/or cut from a unitary flat member or sheet, and then rolled or formed into a tubular structure and subsequently formed and/or heat set to the desired shape in the expanded configuration. Some exemplary means and/or methods of making and/or forming the expandable framework 110 and/or the plurality of interconnected struts 112 include laser cutting, machining, punching, stamping, electro discharge machining (EDM), chemical dissolution, etc. Other means and/or methods are also contemplated.

In some embodiments, the occlusive implant 100 and/or the expandable framework 110 may include a plurality of anchor members 140 projecting radially outward from the plurality of interconnected struts 112 in the expanded configuration. In some embodiments, each anchor member of the plurality of anchor members 140 may include a root portion 142 directly and/or fixedly attached to and/or at the expandable framework 110 and/or the plurality of interconnected struts 112 and extending distally to a trunk portion 144 in the expanded configuration. In some embodiments, the plurality of anchor members 140 may be configured to engage with the lateral wall of the left atrial appendage. Other configurations are also contemplated. Additionally details regarding the plurality of anchor members 140 is discussed below.

Returning to FIG. 3, in some embodiments, the occlusive implant 100 may optionally include an occlusive element 120 connected to, disposed on, disposed over, disposed about, or covering at least a portion of the expandable framework 110 and/or the plurality of interconnected struts 112. In some embodiments, the occlusive element 120 may be connected to, disposed on, disposed over, disposed about, or cover at least a portion of an outer (or outwardly-facing) surface of the expandable framework 110 and/or the plurality of interconnected struts 112. In some embodiments, the occlusive element 120 may be attached to the proximal hub 118 and/or may be attached to the expandable framework 110 at the proximal hub 118. In some embodiments, the occlusive element 120 may extend radially outward from and/or may extend distally from the proximal hub 118. In some embodiments, the occlusive element 120 may be attached and/or secured to the expandable framework 110 at a plurality of discrete locations. In some embodiments, one of, some of, and/or all of the plurality of anchor members 140 may extend through an occlusive element 120, where present.

In some embodiments, the occlusive element 120 may include a membrane, a fabric, a mesh, a tissue element, or another suitable construction. In some embodiments, the occlusive element 120 may be porous. In some embodiments, the occlusive element 120 may be non-porous. In some embodiments, the occlusive element 120 may be permeable to selected gases and/or fluids. In some embodiments, the occlusive element 120 may be substantially impermeable to selected gases and/or fluids, such as blood, water, etc. In some embodiments, the occlusive element 120 may be designed, sized, and/or configured to prevent thrombus and/or embolic material from passing out of the left atrial appendage into the left atrium and/or the patient's bloodstream. In some embodiments, the occlusive element 120 may be configured to promote endothelization after implantation, thereby effectively removing the target site (e.g., the left atrial appendage, etc.) from the patient's circulatory system. Some suitable, but non-limiting, examples of materials for the occlusive element 120 are discussed below.

Figure 5:
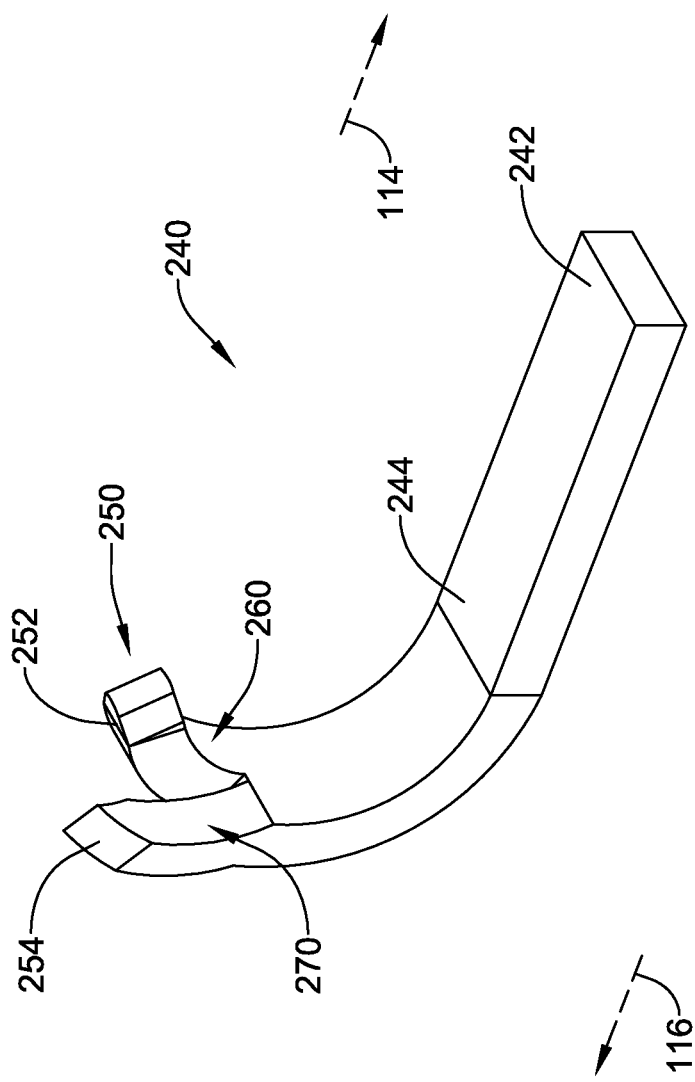
FIG. 5 is a perspective view illustrating an example embodiment of a portion of the occlusive implant of FIGS. 3-4.
Figure 6:
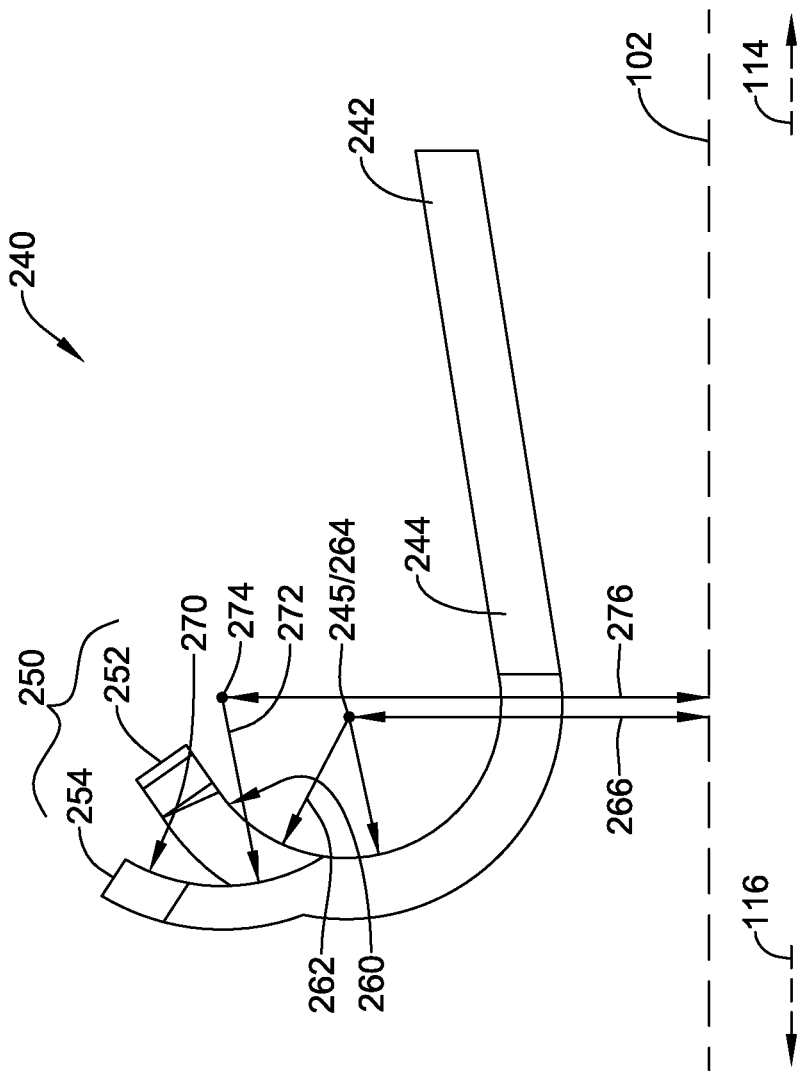
FIG. 6 is a side view illustrating the portion of the occlusive implant of FIG. 5.

FIGS. 5-6 illustrate an example embodiment of one of a plurality of anchor members 240 associated with the occlusive implant 100. As will be understood, the discussion herein related to the plurality of anchor members 240 may be applied equally to and/or may be used in place of each of, some of, or one of the plurality of anchor members 140 shown in FIGS. 3-4, as desired. References to the expandable framework 110 and/or elements thereof discussed herein, while not expressly shown, may be understood to be as shown and/or discussed in the context of FIGS. 3-4.

As discussed herein, the expandable framework 110 may include a plurality of anchor members 240 extending radially outward from the expandable framework 110 in the expanded configuration. In some embodiments, each anchor member of the plurality of anchor members 240 may include a root portion 242 directly and/or fixedly attached to and/or at the expandable framework 110 and/or the plurality of interconnected struts 112 and extending distally to a trunk portion 244 in the expanded configuration. In some embodiments, a proximal trunk portion may extend along and/or generally parallel to the expandable framework 110 in the expanded configuration. In some embodiments, the proximal trunk portion may extend distally from the root portion 242 and generally parallel to the central longitudinal axis 102 of the expandable framework 110. In some embodiments, the proximal trunk portion may extend distally from the root portion 242 and radially inward toward the central longitudinal axis 102 in the expanded configuration. In some embodiments, the proximal trunk portion may extend distally from the root portion 242 and radially outward away from the central longitudinal axis 102 in the expanded configuration. In some embodiments, at least a portion of the trunk portion 244 extends radially outward of and/or relative to the root portion 242 in the expanded configuration. In some embodiments, a distal trunk portion may extend radially outward of and/or relative to the root portion 242 in the expanded configuration. In some embodiments, the distal trunk portion may include a bend extending radially outward from the proximal trunk portion such that at least a portion of the distal trunk portion extends radially outward of and/or relative to the root portion 242 in the expanded configuration.

In some embodiments, at least one of the plurality of anchor members 240 may include a plurality of branches 250 extending radially outward from the trunk portion 244 in the expanded configuration. In some embodiments, a tip portion of each branch of the plurality of branches 250 may extend proximally of and/or from a distalmost portion of its respective branch in the expanded configuration. In some embodiments, the plurality of branches 250 may include a first branch 252 and a second branch 254. The plurality of branches 250 may be circumferentially and/or laterally offset from each other. For example, the first branch 252 may be circumferentially and/or laterally offset from the second branch 254. In at least some embodiments, the second branch 254 is not axially and/or longitudinally aligned with the first branch 252.

In some embodiments, the first branch 252 may include a rounded tip and the second branch 254 may include a sharpened tip. Other configurations are also contemplated. In some embodiments, each branch of the plurality of branches 250 may be configured to penetrate tissue in the expanded configuration. In some embodiments, only the sharpened tip of the second branch 254 may be configured to penetrate tissue in the expanded configuration.

In some embodiments, the first branch 252 may extend proximally more than the second branch 254 as measured parallel to the central longitudinal axis 102 of the expandable framework 110 in the expanded configuration. In some embodiments, the second branch 254 and/or the sharpened tip may be disposed distal of the first branch 252 and/or the rounded tip as measured parallel to the central longitudinal axis 102 of the expandable framework 110 in the expanded configuration.

In some embodiments, the second branch 254 may extend radially outward a greater distance from the central longitudinal axis 102 of the expandable framework 110 and/or the occlusive implant 100 (as measured along a radius in a plane normal to the central longitudinal axis 102) than the first branch 252 in the expanded configuration.

In some embodiments, the first branch 252 of the plurality of branches 250 may be curved in the expanded configuration. In some embodiments, the second branch 254 of the plurality of branches 250 may be curved in the expanded configuration. In some embodiments, each branch of the plurality of branches 250 may be curved in the expanded configuration. In some embodiments, the first branch 252 of the plurality of branches 250 may be curved in a radially outward direction from the trunk portion 244 in the expanded configuration. In some embodiments, the second branch 254 of the plurality of branches 250 may be curved in the radially outward direction from the trunk portion 244 in the expanded configuration. In some embodiments, each branch of the plurality of branches 250 may be curved in the radially outward direction from the trunk portion 244 in the expanded configuration. In some embodiments, the first branch 252 of the plurality of branches 250 may be curved in a proximal direction from the trunk portion 244 in the expanded configuration. In some embodiments, the second branch 254 of the plurality of branches 250 may be curved in the proximal direction from the trunk portion 244 in the expanded configuration. In some embodiments, each branch of the plurality of branches 250 may be curved in the proximal direction from the trunk portion 244 in the expanded configuration.

In some embodiments, at least one branch of the plurality of branches 250 may have a concave cross-section facing toward the proximal end 114 of the expandable framework 110 in the expanded configuration. In some embodiments, the first branch 252 of the plurality of branches 250 may have a concave cross-section facing toward the proximal end 114 of the expandable framework 110 in the expanded configuration. In some embodiments, the second branch 254 of the plurality of branches 250 may have a concave cross-section facing toward the proximal end 114 of the expandable framework 110 in the expanded configuration. In some embodiments, each branch of the plurality of branches 250 may have a concave cross-section facing toward the proximal end 114 of the expandable framework 110 in the expanded configuration.

In some embodiments, the first branch 252 of the plurality of branches 250 may include a proximally facing first curved surface 260 defined by a first radius 262 and a first center 264 in the expanded configuration. In some embodiments, the second branch 254 of the plurality of branches 250 may include a proximally facing second curved surface 270 defined by a second radius 272 and a second center 274 in the expanded configuration. In some embodiments, the second center 274 may be offset radially outward from the first center 264 relative to the central longitudinal axis 102 of the expandable framework 110 in the expanded configuration.

In some embodiments, at least a portion of the trunk portion 244 curves radially outward relative to the root portion 242 in the expanded configuration and is defined by a center 245. In some embodiments, the first center 264 of the first curved surface 260 of the first branch 252 and the center 245 of the at least a portion of the trunk portion 244 that curves radially outward relative to the root portion 242 are disposed a first radial distance 266 from the central longitudinal axis 102 of the expandable framework in the expanded configuration, and the second center 274 of the second curved surface 270 of the second branch 254 is disposed a second radial distance 276 from the central longitudinal axis 102 greater than the first radial distance 266 in the expanded configuration.

Figure 6A:
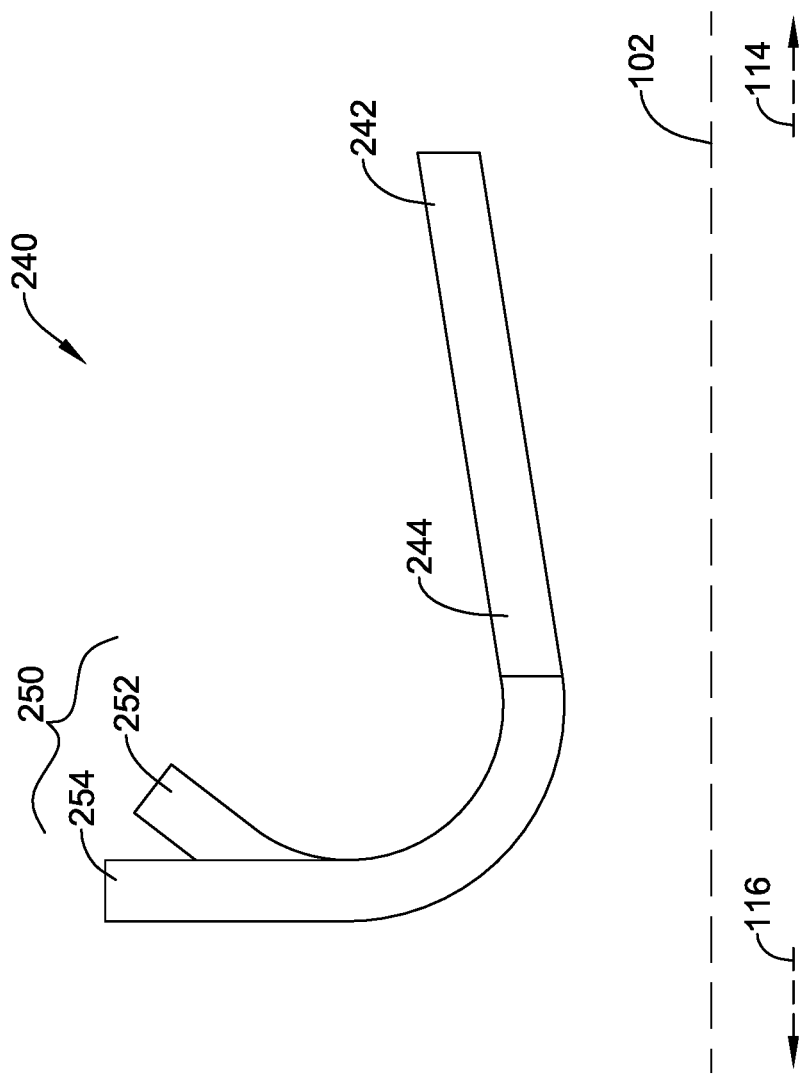
FIG. 6A is a side view illustrating alternative configuration(s) of the portion of the occlusive implant of FIG. 5.

In some alternative embodiments, at least a portion of the first branch 252 and/or the second branch 254 extending radially outward from the at least a portion of the trunk portion 244 that curves radially outward relative to the root portion 242 may be substantially straight and/or may be devoid of a curve, a radius, and/or a defined center, as shown in FIG. 6A. In some embodiments, at least a portion of the first branch 252 extending radially outward from the at least a portion of the trunk portion 244 that curves radially outward relative to the root portion 242 may be substantially straight and/or may be devoid of a curve, a radius, and/or a defined center. In some embodiments, at least a portion of the second branch 254 extending radially outward from the at least a portion of the trunk portion 244 that curves radially outward relative to the root portion 242 may be substantially straight and/or may be devoid of a curve, a radius, and/or a defined center. In some embodiments, at least a portion of both of the first branch 252 and the second branch 254 extending radially outward from the at least a portion of the trunk portion 244 that curves radially outward relative to the root portion 242 may be substantially straight and/or may be devoid of a curve, a radius, and/or a defined center. In some embodiments, a first portion of the first branch 252 may be curved and a second portion of the first branch 252 may be substantially straight. In some embodiments, a first portion of the second branch 254 may be curved and a second portion of the second branch 254 may be substantially straight. Other configurations are also contemplated.

Figure 7:
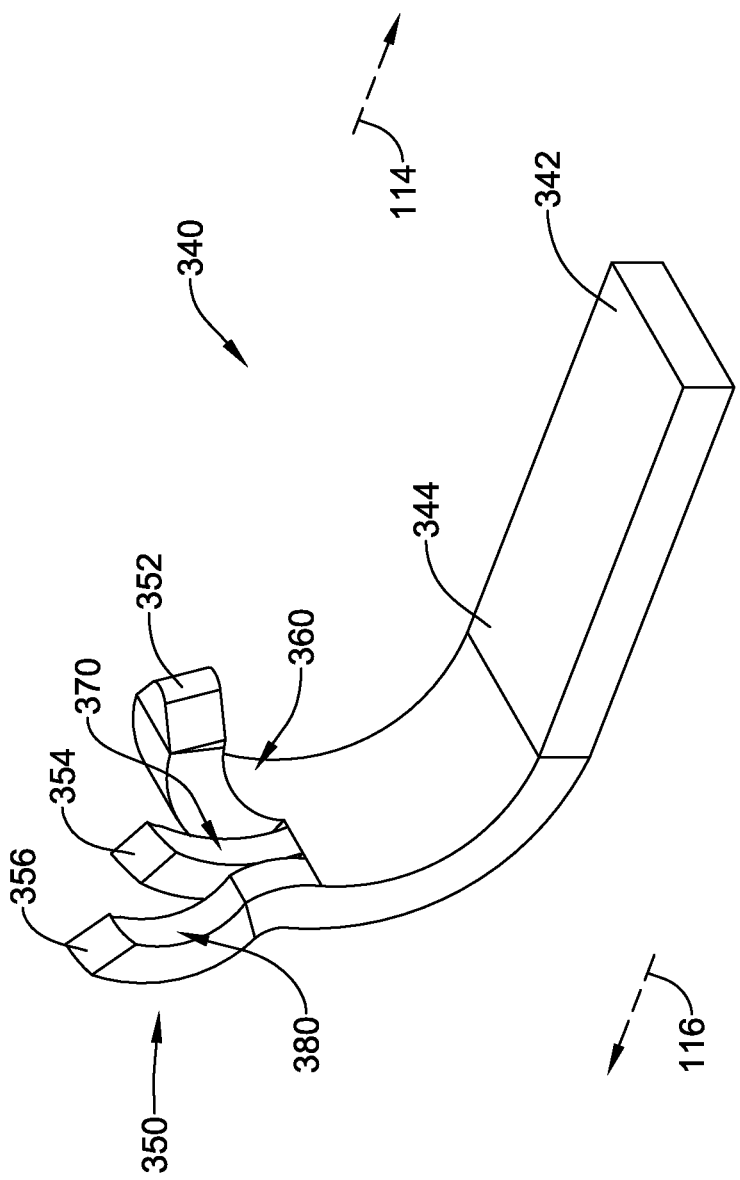
FIG. 7 is a perspective view illustrating an example embodiment of a portion of the occlusive implant of FIGS. 3-4.
Figure 8:
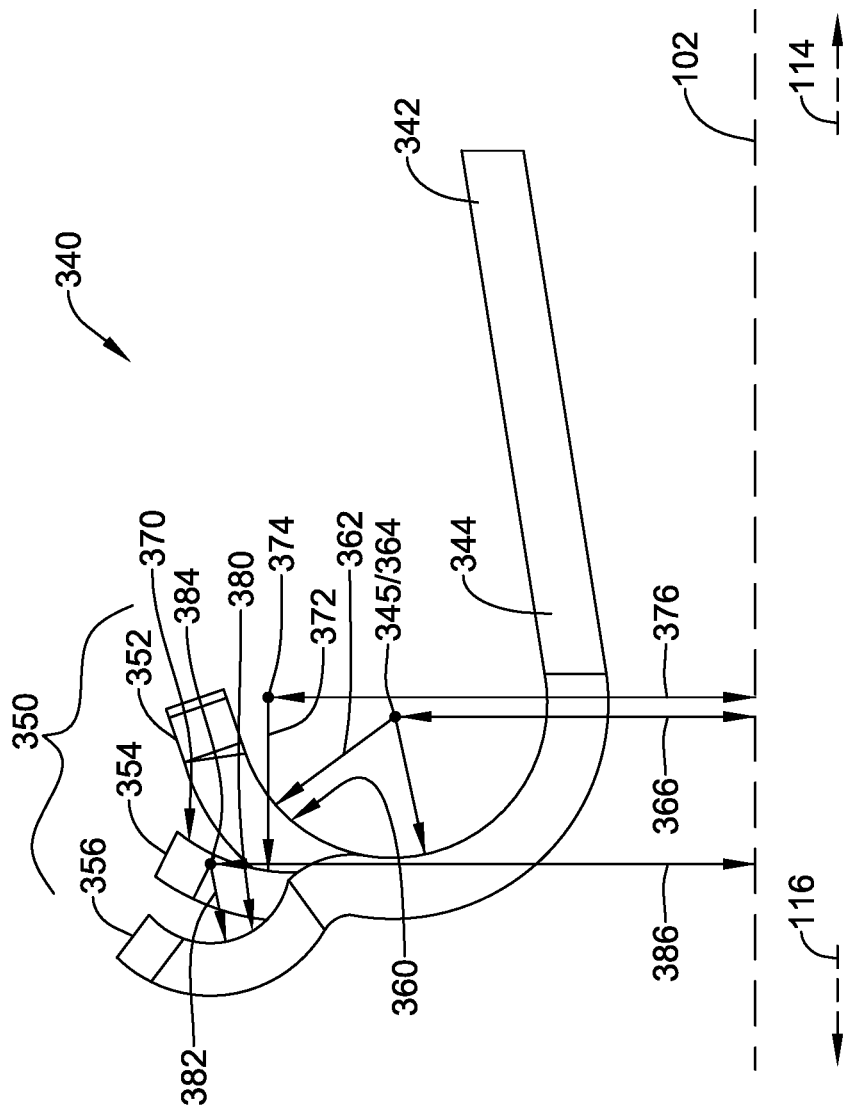
FIG. 8 is a side view illustrating the portion of the occlusive implant of FIG. 7.

FIGS. 7-8 illustrate an example embodiment of one of a plurality of anchor members 340 associated with the occlusive implant 100. As will be understood, the discussion herein related to the plurality of anchor members 340 may be applied equally to and/or may be used in place of each of, some of, or one of the plurality of anchor members 140 shown in FIGS. 3-4, as desired. References to the expandable framework 110 and/or elements thereof discussed herein, while not expressly shown, may be understood to be as shown and/or discussed in the context of FIGS. 3-4.

As discussed herein, the expandable framework 110 may include a plurality of anchor members 340 extending radially outward from the expandable framework 110 in the expanded configuration. In some embodiments, each anchor member of the plurality of anchor members 340 may include a root portion 342 directly and/or fixedly attached to and/or at the expandable framework 110 and/or the plurality of interconnected struts 112 and extending distally to a trunk portion 344 in the expanded configuration. In some embodiments, a proximal trunk portion may extend along and/or generally parallel to the expandable framework 110 in the expanded configuration. In some embodiments, the proximal trunk portion may extend distally from the root portion 342 and generally parallel to the central longitudinal axis 102 of the expandable framework 110. In some embodiments, the proximal trunk portion may extend distally from the root portion 342 and radially inward toward the central longitudinal axis 102 in the expanded configuration. In some embodiments, the proximal trunk portion may extend distally from the root portion 342 and radially outward away from the central longitudinal axis 102 in the expanded configuration. In some embodiments, at least a portion of the trunk portion 344 extends radially outward of and/or relative to the root portion 342 in the expanded configuration. In some embodiments, a distal trunk portion may extend radially outward of and/or relative to the root portion 342 in the expanded configuration. In some embodiments, the distal trunk portion may include a bend extending radially outward from the proximal trunk portion such that at least a portion of the distal trunk portion extends radially outward of and/or relative to the root portion 342 in the expanded configuration.

In some embodiments, at least one of the plurality of anchor members 340 may include a plurality of branches 350 extending radially outward from the trunk portion 344 in the expanded configuration. In some embodiments, a tip portion of each branch of the plurality of branches 350 may extend proximally of and/or from a distalmost portion of its respective branch in the expanded configuration. In some embodiments, the plurality of branches 350 may include a first branch 352 and a second branch 354. In some embodiments, the plurality of branches 350 may further include a third branch 356. The plurality of branches 350 may be circumferentially and/or laterally offset from each other. In some embodiments, the first branch 352 may be circumferentially and/or laterally offset from the second branch 354 and/or the third branch 356. In some embodiments, the second branch 354 may be circumferentially and/or laterally offset from the first branch 352 and/or the third branch 356. In some embodiments, the third branch 356 may be circumferentially and/or laterally offset from the first branch 352 and/or the second branch 354.

In some embodiments, the second branch 354 may be circumferentially and/or laterally offset from the first branch 352 in a first circumferential direction (e.g., counterclockwise as viewed from the proximal end 114 toward the distal end 116 of the expandable framework 110) and/or a first lateral direction. In some embodiments, the third branch 356 may be circumferentially and/or laterally offset from the first branch 352 and/or the second branch 354 in the first circumferential direction and/or the first lateral direction. In some embodiments, the second branch 354 may be disposed circumferentially between the first branch 352 and the third branch 356.

In some embodiments, the first branch 352 is not axially and/or longitudinally aligned with the second branch 354 and/or the third branch 356. In some embodiments, the second branch 354 is not axially and/or longitudinally aligned with the first branch 352 and/or the third branch 356. In some embodiments, the third branch 356 is not axially and/or longitudinally aligned with the first branch 352 and/or the second branch 354. Other configurations are also contemplated.

In some embodiments, at least one of the plurality of branches 350 may include a rounded tip. In some embodiments, at least one of the first branch 352, the second branch 354, and the third branch 356 may include a rounded tip. In some embodiments, other branches of the plurality of branches 350 may each include a sharpened tip. In some embodiments, the first branch 352 may include a rounded tip, the second branch 354 may include a sharpened tip, and the third branch 356 may include a sharpened tip. Other configurations are also contemplated. In some embodiments, each branch of the plurality of branches 350 may be configured to penetrate tissue in the expanded configuration. In some embodiments, only the sharpened tip of the second branch 354 and/or the third branch 356 may be configured to penetrate tissue in the expanded configuration.

In some embodiments, the first branch 352 may extend proximally more than the second branch 354 and/or the third branch 356 as measured parallel to the central longitudinal axis 102 of the expandable framework 110 in the expanded configuration. In some embodiments, the second branch 354, the third branch 356, and/or the sharpened tip(s) thereof may be disposed distal of the first branch 352 and/or the rounded tip as measured parallel to the central longitudinal axis 102 of the expandable framework 110 in the expanded configuration.

In some embodiments, the second branch 354 and/or the third branch 356 may extend radially outward a greater distance from the central longitudinal axis 102 of the expandable framework 110 and/or the occlusive implant 100 (as measured along a radius in a plane normal to the central longitudinal axis 102) than the first branch 352 in the expanded configuration.

In some embodiments, the first branch 352 of the plurality of branches 350 may be curved in the expanded configuration. In some embodiments, the second branch 354 of the plurality of branches 350 may be curved in the expanded configuration. In some embodiments, the third branch 356 of the plurality of branches 350 may be curved in the expanded configuration. In some embodiments, each branch of the plurality of branches 350 may be curved in the expanded configuration. In some embodiments, the first branch 352 of the plurality of branches 350 may be curved in a radially outward direction from the trunk portion 344 in the expanded configuration. In some embodiments, the second branch 354 of the plurality of branches 350 may be curved in the radially outward direction from the trunk portion 344 in the expanded configuration. In some embodiments, the third branch 356 of the plurality of branches 350 may be curved in the radially outward direction from the trunk portion 344 in the expanded configuration. In some embodiments, each branch of the plurality of branches 350 may be curved in the radially outward direction from the trunk portion 344 in the expanded configuration. In some embodiments, the first branch 352 of the plurality of branches 350 may be curved in a proximal direction from the trunk portion 344 in the expanded configuration. In some embodiments, the second branch 354 of the plurality of branches 350 may be curved in the proximal direction from the trunk portion 344 in the expanded configuration. In some embodiments, the third branch 356 of the plurality of branches 350 may be curved in the proximal direction from the trunk portion 344 in the expanded configuration. In some embodiments, each branch of the plurality of branches 350 may be curved in the proximal direction from the trunk portion 344 in the expanded configuration.

In some embodiments, at least one branch of the plurality of branches 350 may have a concave cross-section facing toward the proximal end 114 of the expandable framework 110 in the expanded configuration. In some embodiments, the first branch 352 of the plurality of branches 350 may have a concave cross-section facing toward the proximal end 114 of the expandable framework 110 in the expanded configuration. In some embodiments, the second branch 354 of the plurality of branches 350 may have a concave cross-section facing toward the proximal end 114 of the expandable framework 110 in the expanded configuration. In some embodiments, the third branch 356 of the plurality of branches 350 may have a concave cross-section facing toward the proximal end 114 of the expandable framework 110 in the expanded configuration. In some embodiments, each branch of the plurality of branches 350 may have a concave cross-section facing toward the proximal end 114 of the expandable framework 110 in the expanded configuration.

In some embodiments, the first branch 352 of the plurality of branches 350 may include a proximally facing first curved surface 360 defined by a first radius 362 and a first center 364 in the expanded configuration. In some embodiments, the second branch 354 of the plurality of branches 350 may include a proximally facing second curved surface 370 defined by a second radius 372 and a second center 374 in the expanded configuration. In some embodiments, the third branch 356 of the plurality of branches 350 may include a proximally facing third curved surface 380 defined by a third radius 382 and a third center 384 in the expanded configuration. In some embodiments, the second center 374 may be offset radially outward from the first center 364 relative to the central longitudinal axis 102 of the expandable framework 110 in the expanded configuration. In some embodiments, the third center 384 may be offset radially outward from the first center 364 and/or the second center 374 relative to the central longitudinal axis 102 of the expandable framework 110 in the expanded configuration.

In some embodiments, at least a portion of the trunk portion 344 curves radially outward relative to the root portion 342 in the expanded configuration and is defined by a center 345. In some embodiments, the first center 364 of the first curved surface 360 of the first branch 352 and the center 345 of the at least a portion of the trunk portion 344 that curves radially outward relative to the root portion 342 are disposed a first radial distance 366 from the central longitudinal axis 102 of the expandable framework in the expanded configuration, and the second center 374 of the second curved surface 370 of the second branch 354 is disposed a second radial distance 376 from the central longitudinal axis 102 greater than the first radial distance 366 in the expanded configuration. In some embodiments, the third center 384 of the third curved surface 380 of the third branch 356 is disposed a third radial distance 386 from the central longitudinal axis 102 greater than the first radial distance 366 and/or the second radial distance 376 in the expanded configuration.

In some alternative embodiments, at least a portion of the first branch 352, the second branch 354, and/or the third branch 356 extending radially outward from the at least a portion of the trunk portion 344 that curves radially outward relative to the root portion 342 may be substantially straight and/or may be devoid of a curve, a radius, and/or a defined center, similar to the alternative embodiment(s) shown in FIG. 6A.

Figure 9:
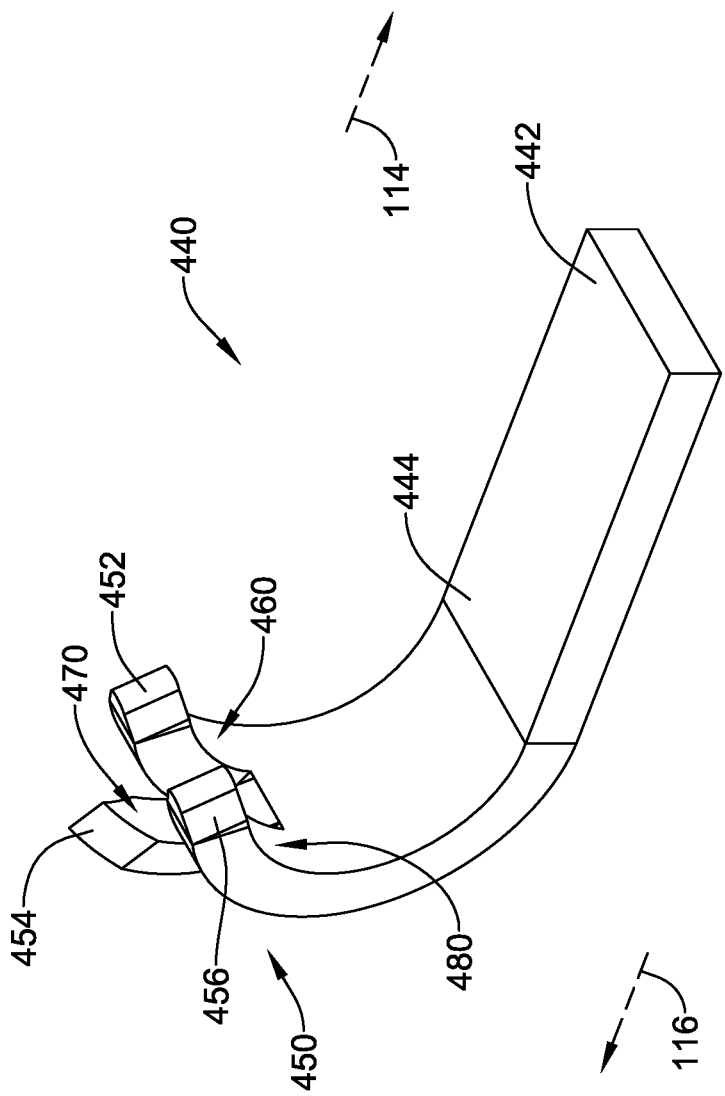
FIG. 9 is a perspective view illustrating an example embodiment of a portion of the occlusive implant of FIGS. 3-4.
Figure 10:
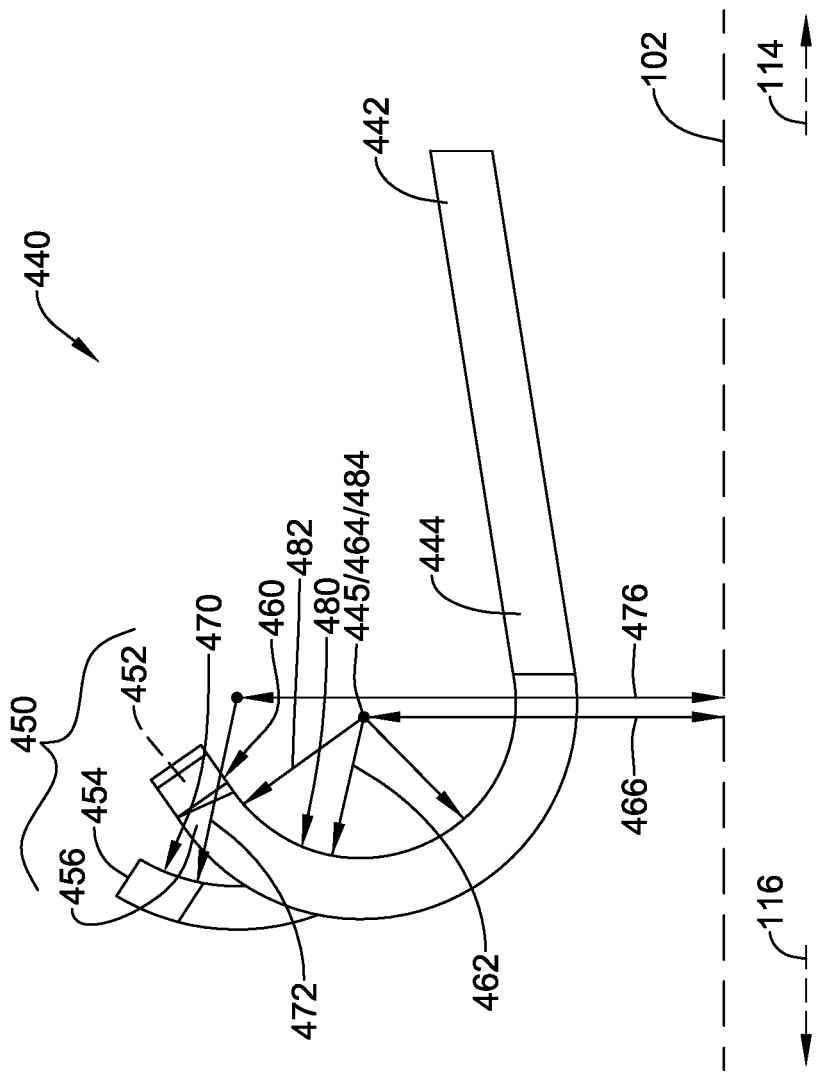
FIG. 10 is a side view illustrating the portion of the occlusive implant of FIG. 9.

FIGS. 9-10 illustrate an example embodiment of one of a plurality of anchor members 440 associated with the occlusive implant 100. As will be understood, the discussion herein related to the plurality of anchor members 440 may be applied equally to and/or may be used in place of each of, some of, or one of the plurality of anchor members 140 shown in FIGS. 3-4, as desired. References to the expandable framework 110 and/or elements thereof discussed herein, while not expressly shown, may be understood to be as shown and/or discussed in the context of FIGS. 3-4.

As discussed herein, the expandable framework 110 may include a plurality of anchor members 440 extending radially outward from the expandable framework 110 in the expanded configuration. In some embodiments, each anchor member of the plurality of anchor members 440 may include a root portion 442 directly and/or fixedly attached to and/or at the expandable framework 110 and/or the plurality of interconnected struts 112 and extending distally to a trunk portion 444 in the expanded configuration. In some embodiments, a proximal trunk portion may extend along and/or generally parallel to the expandable framework 110 in the expanded configuration. In some embodiments, the proximal trunk portion may extend distally from the root portion 442 and generally parallel to the central longitudinal axis 102 of the expandable framework 110. In some embodiments, the proximal trunk portion may extend distally from the root portion 442 and radially inward toward the central longitudinal axis 102 in the expanded configuration. In some embodiments, the proximal trunk portion may extend distally from the root portion 442 and radially outward away from the central longitudinal axis 102 in the expanded configuration. In some embodiments, at least a portion of the trunk portion 444 extends radially outward of and/or relative to the root portion 442 in the expanded configuration. In some embodiments, a distal trunk portion may extend radially outward of and/or relative to the root portion 442 in the expanded configuration. In some embodiments, the distal trunk portion may include a bend extending radially outward from the proximal trunk portion such that at least a portion of the distal trunk portion extends radially outward of and/or relative to the root portion 442 in the expanded configuration.

In some embodiments, at least one of the plurality of anchor members 440 may include a plurality of branches 450 extending radially outward from the trunk portion 444 in the expanded configuration. In some embodiments, a tip portion of each branch of the plurality of branches 450 may extend proximally of and/or from a distalmost portion of its respective branch in the expanded configuration. In some embodiments, the plurality of branches 450 may include a first branch 452 and a second branch 454. In some embodiments, the plurality of branches 450 may further include a third branch 456. The plurality of branches 450 may be circumferentially and/or laterally offset from each other. In some embodiments, the first branch 452 may be circumferentially and/or laterally offset from the second branch 454 and/or the third branch 456. In some embodiments, the second branch 454 may be circumferentially and/or laterally offset from the first branch 452 and/or the third branch 456. In some embodiments, the third branch 456 may be circumferentially and/or laterally offset from the first branch 452 and/or the second branch 454.

In some embodiments, the second branch 454 may be circumferentially and/or laterally offset from the first branch 452 in a first circumferential direction (e.g., counterclockwise as viewed from the proximal end 114 toward the distal end 116 of the expandable framework 110) and/or a first lateral direction. In some embodiments, the third branch 456 may be circumferentially and/or laterally offset from the first branch 452 and/or the second branch 454 in the first circumferential direction and/or the first lateral direction. In some embodiments, the second branch 454 may be disposed circumferentially between the first branch 452 and the third branch 456.

In some embodiments, the first branch 452 is not axially and/or longitudinally aligned with the second branch 454 and/or the third branch 456. In some embodiments, the second branch 454 is not axially and/or longitudinally aligned with the first branch 452 and/or the third branch 456. In some embodiments, the third branch 456 is not axially and/or longitudinally aligned with the first branch 452 and/or the second branch 454. Other configurations are also contemplated.

In some embodiments, at least one of the plurality of branches 450 may include a rounded tip. In some embodiments, at least one of the first branch 452, the second branch 454, and the third branch 456 may include a rounded tip. In some embodiments, other branches of the plurality of branches 450 may each include a sharpened tip. In some embodiments, the first branch 452 may include a rounded tip, the second branch 454 may include a sharpened tip, and the third branch 456 may include a rounded tip. Other configurations are also contemplated. In some embodiments, each branch of the plurality of branches 450 may be configured to penetrate tissue in the expanded configuration. In some embodiments, only the sharpened tip of the second branch 454 may be configured to penetrate tissue in the expanded configuration.

In some embodiments, the first branch 452 and/or the third branch 456 may extend proximally more than the second branch 454 as measured parallel to the central longitudinal axis 102 of the expandable framework 110 in the expanded configuration. In some embodiments, the second branch 454 and/or the sharpened tip thereof may be disposed distal of the first branch 452 and/or the third branch 456 and/or the rounded tip(s) thereof as measured parallel to the central longitudinal axis 102 of the expandable framework 110 in the expanded configuration.

In some embodiments, the second branch 454 may extend radially outward a greater distance from the central longitudinal axis 102 of the expandable framework 110 and/or the occlusive implant 100 (as measured along a radius in a plane normal to the central longitudinal axis 102) than the first branch 452 and/or the third branch 456 in the expanded configuration.

In some embodiments, the first branch 452 of the plurality of branches 450 may be curved in the expanded configuration. In some embodiments, the second branch 454 of the plurality of branches 450 may be curved in the expanded configuration. In some embodiments, the third branch 456 of the plurality of branches 450 may be curved in the expanded configuration. In some embodiments, each branch of the plurality of branches 450 may be curved in the expanded configuration. In some embodiments, the first branch 452 of the plurality of branches 450 may be curved in a radially outward direction from the trunk portion 444 in the expanded configuration. In some embodiments, the second branch 454 of the plurality of branches 450 may be curved in the radially outward direction from the trunk portion 444 in the expanded configuration. In some embodiments, the third branch 456 of the plurality of branches 450 may be curved in the radially outward direction from the trunk portion 444 in the expanded configuration. In some embodiments, each branch of the plurality of branches 450 may be curved in the radially outward direction from the trunk portion 444 in the expanded configuration. In some embodiments, the first branch 452 of the plurality of branches 450 may be curved in a proximal direction from the trunk portion 444 in the expanded configuration. In some embodiments, the second branch 454 of the plurality of branches 450 may be curved in the proximal direction from the trunk portion 444 in the expanded configuration. In some embodiments, the third branch 456 of the plurality of branches 450 may be curved in the proximal direction from the trunk portion 444 in the expanded configuration. In some embodiments, each branch of the plurality of branches 450 may be curved in the proximal direction from the trunk portion 444 in the expanded configuration.

In some embodiments, at least one branch of the plurality of branches 450 may have a concave cross-section facing toward the proximal end 114 of the expandable framework 110 in the expanded configuration. In some embodiments, the first branch 452 of the plurality of branches 450 may have a concave cross-section facing toward the proximal end 114 of the expandable framework 110 in the expanded configuration. In some embodiments, the second branch 454 of the plurality of branches 450 may have a concave cross-section facing toward the proximal end 114 of the expandable framework 110 in the expanded configuration. In some embodiments, the third branch 456 of the plurality of branches 450 may have a concave cross-section facing toward the proximal end 114 of the expandable framework 110 in the expanded configuration. In some embodiments, each branch of the plurality of branches 450 may have a concave cross-section facing toward the proximal end 114 of the expandable framework 110 in the expanded configuration.

In some embodiments, the first branch 452 of the plurality of branches 450 may include a proximally facing first curved surface 460 defined by a first radius 462 and a first center 464 in the expanded configuration. In some embodiments, the second branch 454 of the plurality of branches 450 may include a proximally facing second curved surface 470 defined by a second radius 472 and a second center 474 in the expanded configuration. In some embodiments, the third branch 456 of the plurality of branches 450 may include a proximally facing third curved surface 480 defined by a third radius 482 and a third center 484 in the expanded configuration. In some embodiments, the second center 474 may be offset radially outward from the first center 464 and/or the third center 484 relative to the central longitudinal axis 102 of the expandable framework 110 in the expanded configuration.

In some embodiments, at least a portion of the trunk portion 444 curves radially outward relative to the root portion 442 in the expanded configuration and is defined by a center 445. In some embodiments, the first center 464 of the first curved surface 460 of the first branch 452, the third center 484 of the third curved surface 480 of the third branch 456, and the center 445 of the at least a portion of the trunk portion 444 that curves radially outward relative to the root portion 442 are disposed a first radial distance 466 from the central longitudinal axis 102 of the expandable framework 110 in the expanded configuration, and the second center 474 of the second curved surface 470 of the second branch 454 is disposed a second radial distance 476 from the central longitudinal axis 102 greater than the first radial distance 466 in the expanded configuration.

In some alternative embodiments, at least a portion of the first branch 452, the second branch 454, and/or the third branch 456 extending radially outward from the at least a portion of the trunk portion 444 that curves radially outward relative to the root portion 442 may be substantially straight and/or may be devoid of a curve, a radius, and/or a defined center, similar to the alternative embodiment(s) shown in FIG. 6A.

Figure 11:
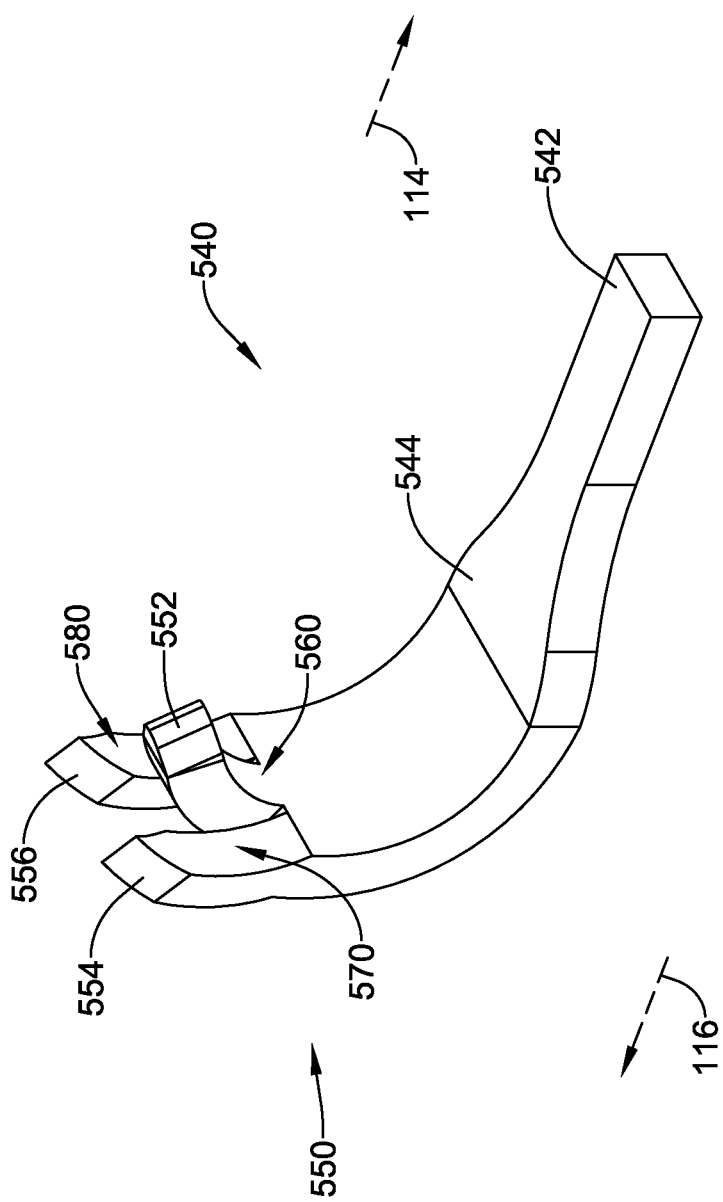
FIG. 11 is a perspective view illustrating an example embodiment of a portion of the occlusive implant of FIGS. 3-4.
Figure 12:
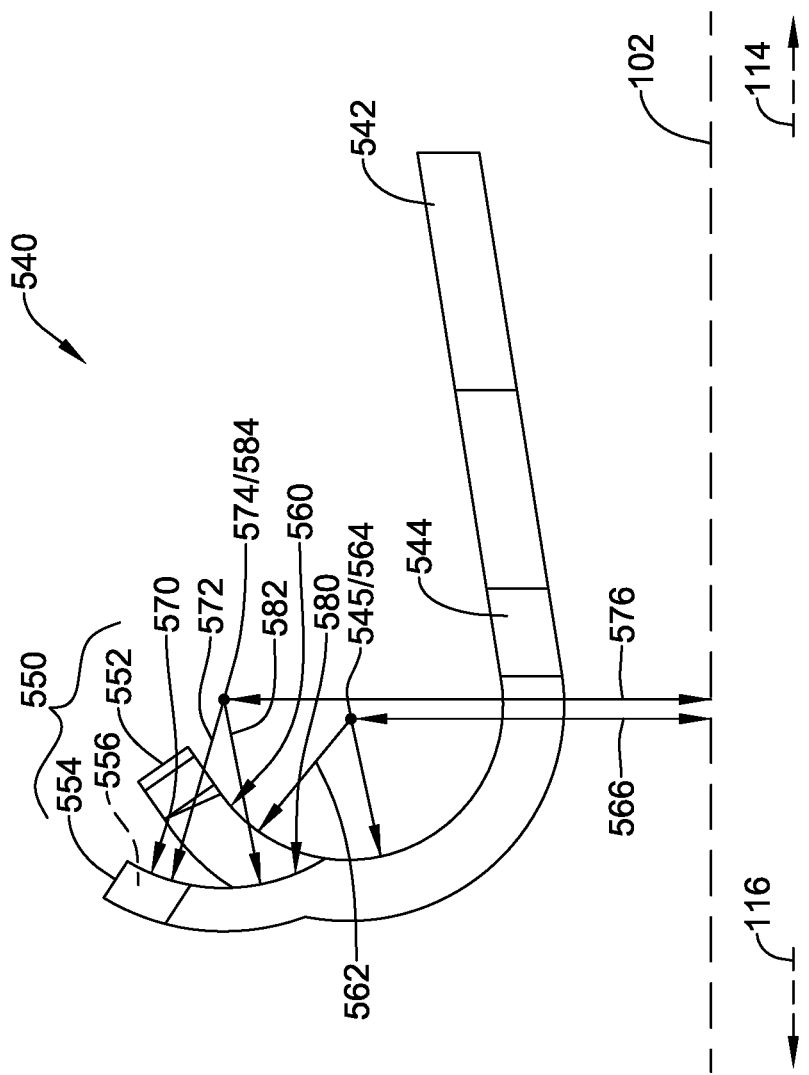
FIG. 12 is a side view illustrating the portion of the occlusive implant of FIG. 11.

FIGS. 11-12 illustrate an example embodiment of one of a plurality of anchor members 540 associated with the occlusive implant 100. As will be understood, the discussion herein related to the plurality of anchor members 540 may be applied equally to and/or may be used in place of each of, some of, or one of the plurality of anchor members 140 shown in FIGS. 3-4, as desired. References to the expandable framework 110 and/or elements thereof discussed herein, while not expressly shown, may be understood to be as shown and/or discussed in the context of FIGS. 3-4.

As discussed herein, the expandable framework 110 may include a plurality of anchor members 540 extending radially outward from the expandable framework 110 in the expanded configuration. In some embodiments, each anchor member of the plurality of anchor members 540 may include a root portion 542 directly and/or fixedly attached to and/or at the expandable framework 110 and/or the plurality of interconnected struts 112 and extending distally to a trunk portion 544 in the expanded configuration. In some embodiments, a proximal trunk portion may extend along and/or generally parallel to the expandable framework 110 in the expanded configuration. In some embodiments, the proximal trunk portion may extend distally from the root portion 542 and generally parallel to the central longitudinal axis 102 of the expandable framework 110. In some embodiments, the proximal trunk portion may extend distally from the root portion 542 and radially inward toward the central longitudinal axis 102 in the expanded configuration. In some embodiments, the proximal trunk portion may extend distally from the root portion 542 and radially outward away from the central longitudinal axis 102 in the expanded configuration. In some embodiments, at least a portion of the trunk portion 544 extends radially outward of and/or relative to the root portion 542 in the expanded configuration. In some embodiments, a distal trunk portion may extend radially outward of and/or relative to the root portion 542 in the expanded configuration. In some embodiments, the distal trunk portion may include a bend extending radially outward from the proximal trunk portion such that at least a portion of the distal trunk portion extends radially outward of and/or relative to the root portion 542 in the expanded configuration.

In some embodiments, at least one of the plurality of anchor members 540 may include a plurality of branches 550 extending radially outward from the trunk portion 544 in the expanded configuration. In some embodiments, a tip portion of each branch of the plurality of branches 550 may extend proximally of and/or from a distalmost portion of its respective branch in the expanded configuration. In some embodiments, the plurality of branches 550 may include a first branch 552 and a second branch 554. In some embodiments, the plurality of branches 550 may further include a third branch 556. The plurality of branches 550 may be circumferentially and/or laterally offset from each other. In some embodiments, the first branch 552 may be circumferentially and/or laterally offset from the second branch 554 and/or the third branch 556. In some embodiments, the second branch 554 may be circumferentially and/or laterally offset from the first branch 552 and/or the third branch 556. In some embodiments, the third branch 556 may be circumferentially and/or laterally offset from the first branch 552 and/or the second branch 554.

In some embodiments, the second branch 554 may be circumferentially and/or laterally offset from the first branch 552 in a first circumferential direction (e.g., counterclockwise as viewed from the proximal end 114 toward the distal end 116 of the expandable framework 110) and/or a first lateral direction. In some embodiments, the third branch 556 may be circumferentially and/or laterally offset from the first branch 552 and/or the second branch 554 in a second circumferential direction opposite the first circumferential direction (e.g., clockwise as viewed from the proximal end 114 toward the distal end 116 of the expandable framework 110) and/or in a second lateral direction opposite the first lateral direction. In some embodiments, the first branch 552 may be disposed circumferentially between the second branch 554 and the third branch 556.

In some embodiments, the first branch 552 is not axially and/or longitudinally aligned with the second branch 554 and/or the third branch 556. In some embodiments, the second branch 554 is not axially and/or longitudinally aligned with the first branch 552 and/or the third branch 556. In some embodiments, the third branch 556 is not axially and/or longitudinally aligned with the first branch 552 and/or the second branch 554. Other configurations are also contemplated.

In some embodiments, at least one of the plurality of branches 550 may include a rounded tip. In some embodiments, at least one of the first branch 552, the second branch 554, and the third branch 556 may include a rounded tip. In some embodiments, other branches of the plurality of branches 550 may each include a sharpened tip. In some embodiments, the first branch 552 may include a rounded tip, the second branch 554 may include a sharpened tip, and the third branch 556 may include a sharpened tip. Other configurations are also contemplated. In some embodiments, each branch of the plurality of branches 550 may be configured to penetrate tissue in the expanded configuration. In some embodiments, only the sharpened tip of the second branch 554 and/or the third branch 556 may be configured to penetrate tissue in the expanded configuration.

In some embodiments, the first branch 552 may extend proximally more than the second branch 554 and/or the third branch 556 as measured parallel to the central longitudinal axis 102 of the expandable framework 110 in the expanded configuration. In some embodiments, the second branch 554, the third branch 556, and/or the sharpened tip(s) thereof may be disposed distal of the first branch 552 and/or the rounded tip thereof as measured parallel to the central longitudinal axis 102 of the expandable framework 110 in the expanded configuration.

In some embodiments, the second branch 554 and/or the third branch 556 may extend radially outward a greater distance from the central longitudinal axis 102 of the expandable framework 110 and/or the occlusive implant 100 (as measured along a radius in a plane normal to the central longitudinal axis 102) than the first branch 552 in the expanded configuration.

In some embodiments, the first branch 552 of the plurality of branches 550 may be curved in the expanded configuration. In some embodiments, the second branch 554 of the plurality of branches 550 may be curved in the expanded configuration. In some embodiments, the third branch 556 of the plurality of branches 550 may be curved in the expanded configuration. In some embodiments, each branch of the plurality of branches 550 may be curved in the expanded configuration. In some embodiments, the first branch 552 of the plurality of branches 550 may be curved in a radially outward direction from the trunk portion 544 in the expanded configuration. In some embodiments, the second branch 554 of the plurality of branches 550 may be curved in the radially outward direction from the trunk portion 544 in the expanded configuration. In some embodiments, the third branch 556 of the plurality of branches 550 may be curved in the radially outward direction from the trunk portion 544 in the expanded configuration. In some embodiments, each branch of the plurality of branches 550 may be curved in the radially outward direction from the trunk portion 544 in the expanded configuration. In some embodiments, the first branch 552 of the plurality of branches 550 may be curved in a proximal direction from the trunk portion 544 in the expanded configuration. In some embodiments, the second branch 554 of the plurality of branches 550 may be curved in the proximal direction from the trunk portion 544 in the expanded configuration. In some embodiments, the third branch 556 of the plurality of branches 550 may be curved in the proximal direction from the trunk portion 544 in the expanded configuration. In some embodiments, each branch of the plurality of branches 550 may be curved in the proximal direction from the trunk portion 544 in the expanded configuration.

In some embodiments, at least one branch of the plurality of branches 550 may have a concave cross-section facing toward the proximal end 114 of the expandable framework 110 in the expanded configuration. In some embodiments, the first branch 552 of the plurality of branches 550 may have a concave cross-section facing toward the proximal end 114 of the expandable framework 110 in the expanded configuration. In some embodiments, the second branch 554 of the plurality of branches 550 may have a concave cross-section facing toward the proximal end 114 of the expandable framework 110 in the expanded configuration. In some embodiments, the third branch 556 of the plurality of branches 550 may have a concave cross-section facing toward the proximal end 114 of the expandable framework 110 in the expanded configuration. In some embodiments, each branch of the plurality of branches 550 may have a concave cross-section facing toward the proximal end 114 of the expandable framework 110 in the expanded configuration.

In some embodiments, the first branch 552 of the plurality of branches 550 may include a proximally facing first curved surface 560 defined by a first radius 562 and a first center 564 in the expanded configuration. In some embodiments, the second branch 554 of the plurality of branches 550 may include a proximally facing second curved surface 570 defined by a second radius 572 and a second center 574 in the expanded configuration. In some embodiments, the third branch 556 of the plurality of branches 550 may include a proximally facing third curved surface 580 defined by a third radius 582 and a third center 584 in the expanded configuration. In some embodiments, the second center 574 and/or the third center 584 may be offset radially outward from the first center 564 relative to the central longitudinal axis 102 of the expandable framework 110 in the expanded configuration.

In some embodiments, at least a portion of the trunk portion 544 curves radially outward relative to the root portion 542 in the expanded configuration and is defined by a center 545. In some embodiments, the first center 564 of the first curved surface 560 of the first branch 552 and the center 545 of the at least a portion of the trunk portion 544 that curves radially outward relative to the root portion 542 are disposed a first radial distance 566 from the central longitudinal axis 102 of the expandable framework in the expanded configuration, and the second center 574 of the second curved surface 570 of the second branch 554 and the third center 584 of the third curved surface 580 of the third branch 556 is disposed a second radial distance 576 from the central longitudinal axis 102 greater than the first radial distance 566 in the expanded configuration.

In some alternative embodiments, at least a portion of the first branch 552, the second branch 554, and/or the third branch 556 extending radially outward from the at least a portion of the trunk portion 544 that curves radially outward relative to the root portion 542 may be substantially straight and/or may be devoid of a curve, a radius, and/or a defined center, similar to the alternative embodiment(s) shown in FIG. 6A.

FIGS. 13A-13D illustrate aspects of the occlusive implant system 10 during capture and/or recapture of the occlusive implant 100. As will be understood, the following discussion shows and refers to one of the plurality of anchor members 240 for ease of understanding. However, it shall be understood that any of the plurality of anchor members 340, 440, 540 described herein may be applied equally to and/or may be used in place of the plurality of anchor members 240 shown in FIGS. 13A-13D, as desired. References to the expandable framework 110 and/or elements thereof discussed herein, while not expressly shown, may be understood to be as shown and/or discussed in the context of FIGS. 3-4.

FIGS. 13A-13D show the sheath 40 disposed alongside and/or radially outward of the occlusive implant 100 (not expressly shown but represented by the plurality of anchor members 240). As discussed herein, the plurality of anchor members 240 may extend radially outward from the expandable framework 110 in the expanded configuration. In at least some embodiments, capturing and/or recapturing the occlusive implant 100 within the implant containment area of the sheath 40 after shifting the expandable framework 110 and/or the occlusive implant 100 to the expanded configuration may include advancing the distal end of the sheath 40 distally into contact with the plurality of anchor members 240 and/or withdrawing the expandable framework 110 and/or the occlusive implant 100 proximally relative to the sheath 40 (using the core wire 30, for example). Contact between the distal end of the sheath 40 and at least one of the plurality of branches 250 may urge remaining branches of the plurality of branches 250 away from contact with the sheath 40, as shown in FIGS. 13A-13D. In some embodiments, contact between the distal end of the sheath 40 and the first branch 252 of the plurality of branches 250 urges the second branch 254 away from contact with the sheath 40.

Figure 13A:
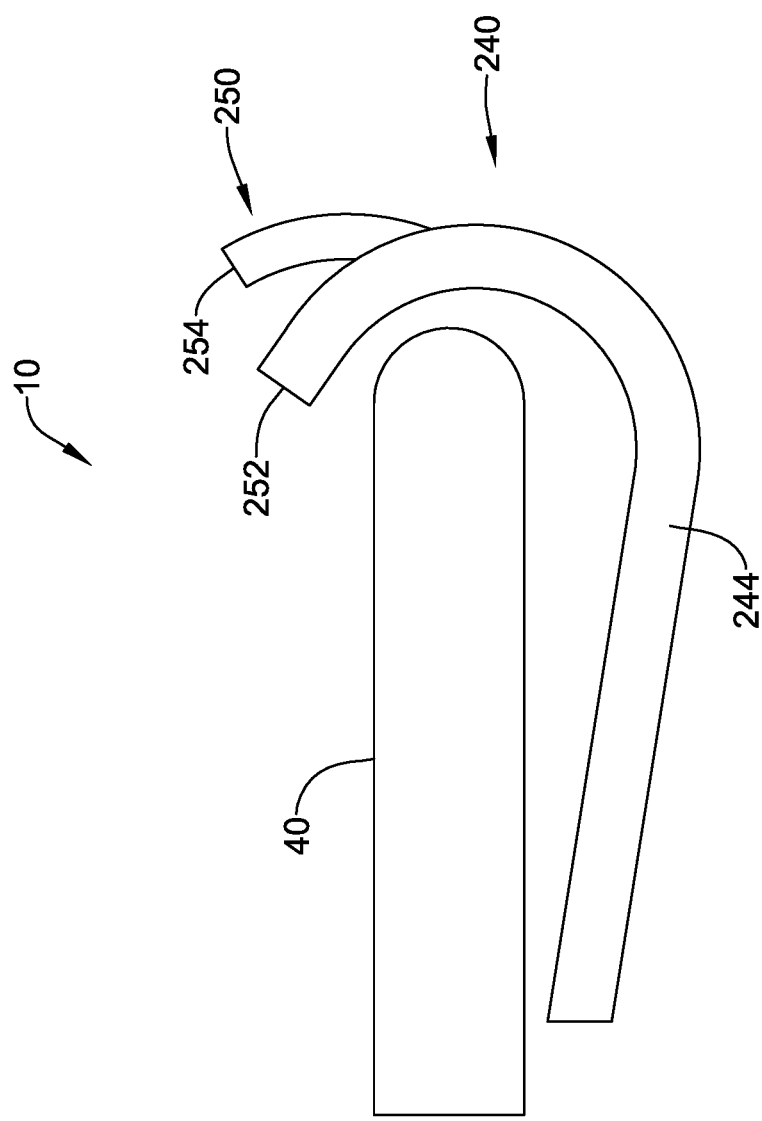
FIGS. 13A-13D illustrate the interaction between selected elements of the occlusive implant system of FIGS. 1-2 during capture and/or recapture of the occlusive implant.
Figure 13B:
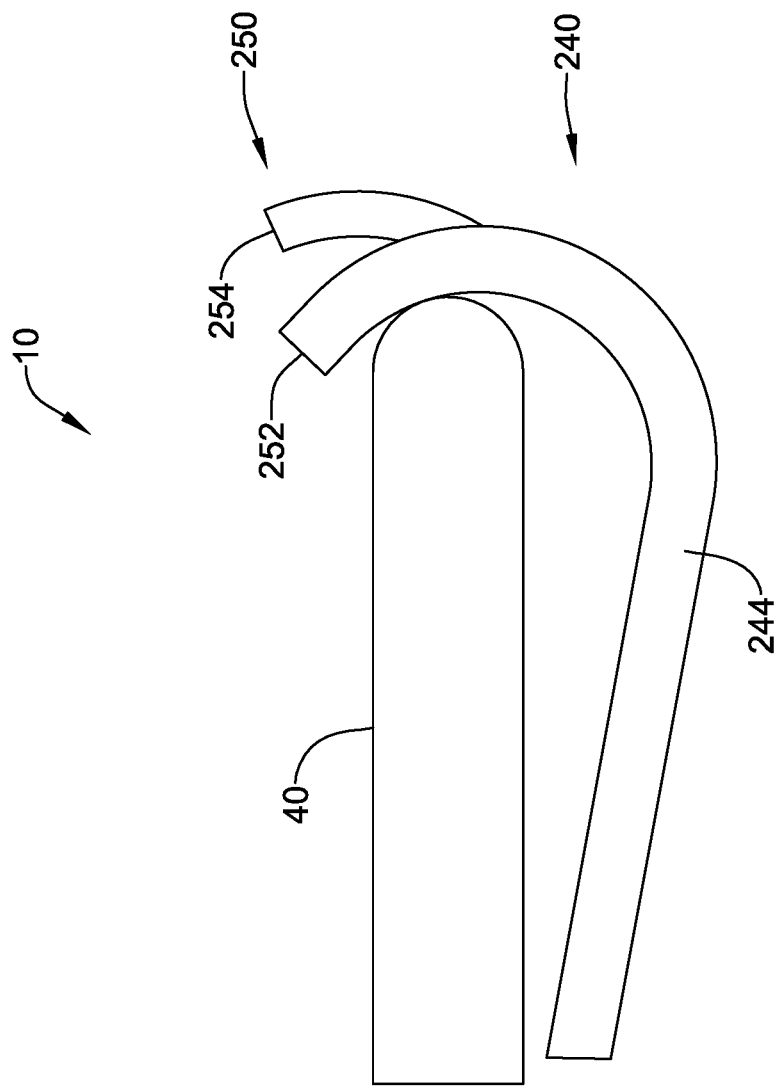
Figure 13C:
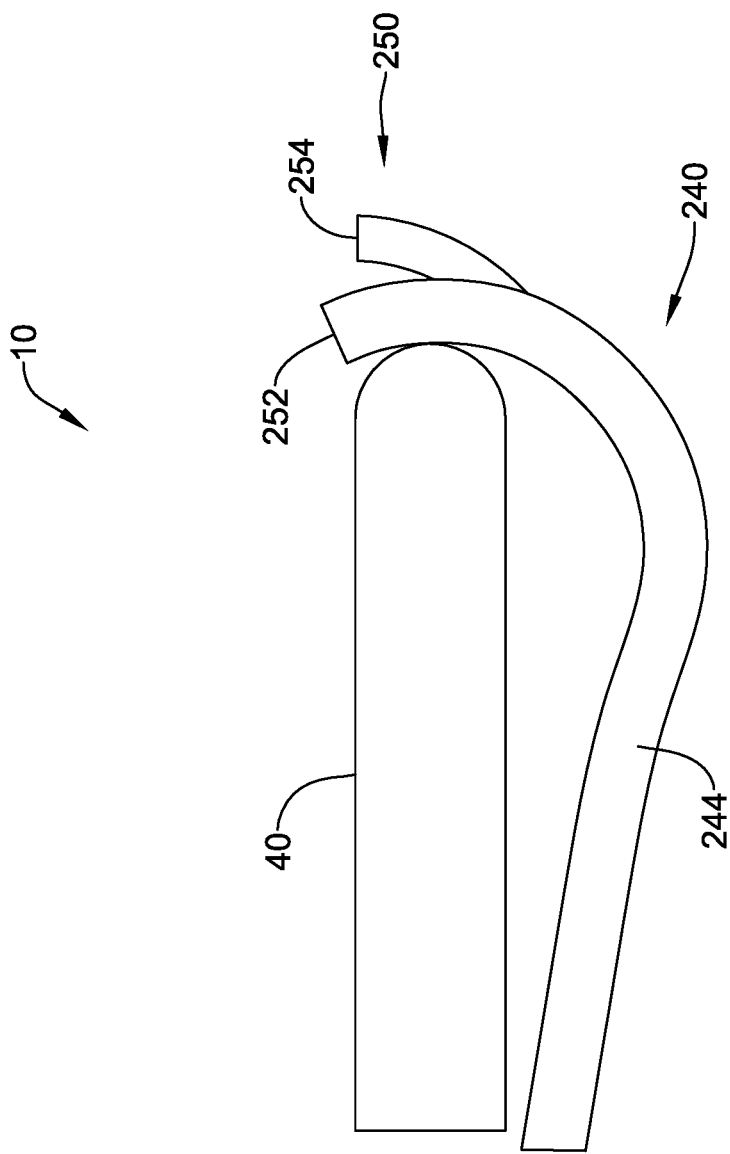
Figure 13D:
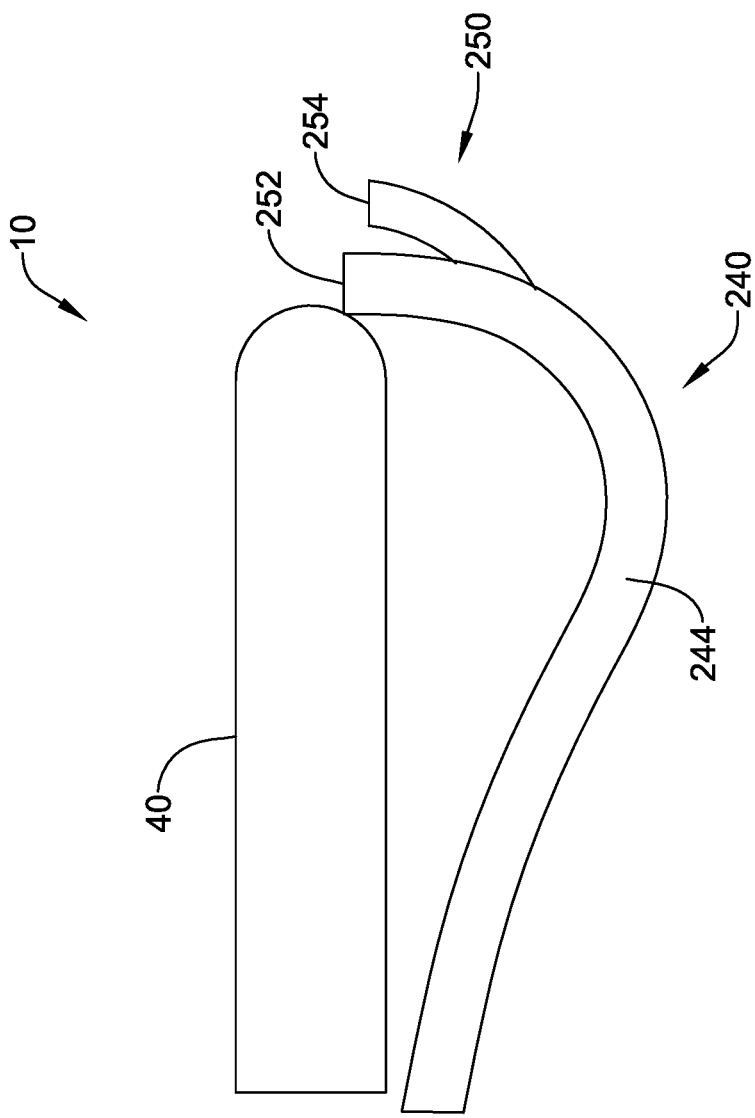

In at least some embodiments, each branch of the plurality of branches 250 contacted by the distal end of the sheath 40 includes a rounded tip and each remaining branch of the plurality of branches 250 includes a sharpened tip. In some embodiments, each sharpened tip is disposed distal of each rounded tip as measured parallel to the central longitudinal axis 102 of the expandable framework 110. In some embodiments, distal advancement of the sheath 40 relative to the expandable framework 110 and/or the occlusive implant 100, and/or proximal withdrawal of the expandable framework 110 and/or the occlusive implant 100 relative to the distal end of the sheath 40, after contact between the distal end of the sheath 40 and at least one of the plurality of branches 250 deflects the at least one of the plurality of anchor members 240 at the trunk portion 244, as seen in FIGS. 13B-13D. The above-described behavior may permit the sharpened tip(s) of the plurality of anchor members 240 to enhance anchoring within the tissue of the patient while preventing contact with the sheath 40 during recapture, which may cause damage and/or increased stress and/or forces within the occlusive implant 100 and/or the occlusive implant system 10.

In some embodiments, after recapture of the occlusive implant 100 within the implant containment area of the sheath 40, the first branch 252 may be disposed more proximally than the second branch 254 as measured parallel to the central longitudinal axis 102 of the expandable framework 110. In some embodiments, after recapture of the occlusive implant 100 within the implant containment area of the sheath 40, the second branch 254 and/or the sharpened tip thereof may be disposed distal of the first branch 252 and/or the rounded tip thereof as measured parallel to the central longitudinal axis 102 of the expandable framework 110. In some embodiments, after recapture of the occlusive implant 100 within the implant containment area of the sheath 40, the first branch 252 may extend radially outward a greater distance from the central longitudinal axis 102 of the expandable framework 110 and/or the occlusive implant 100 (as measured along a radius in a plane normal to the central longitudinal axis 102) than the second branch 254.

Figure 14:
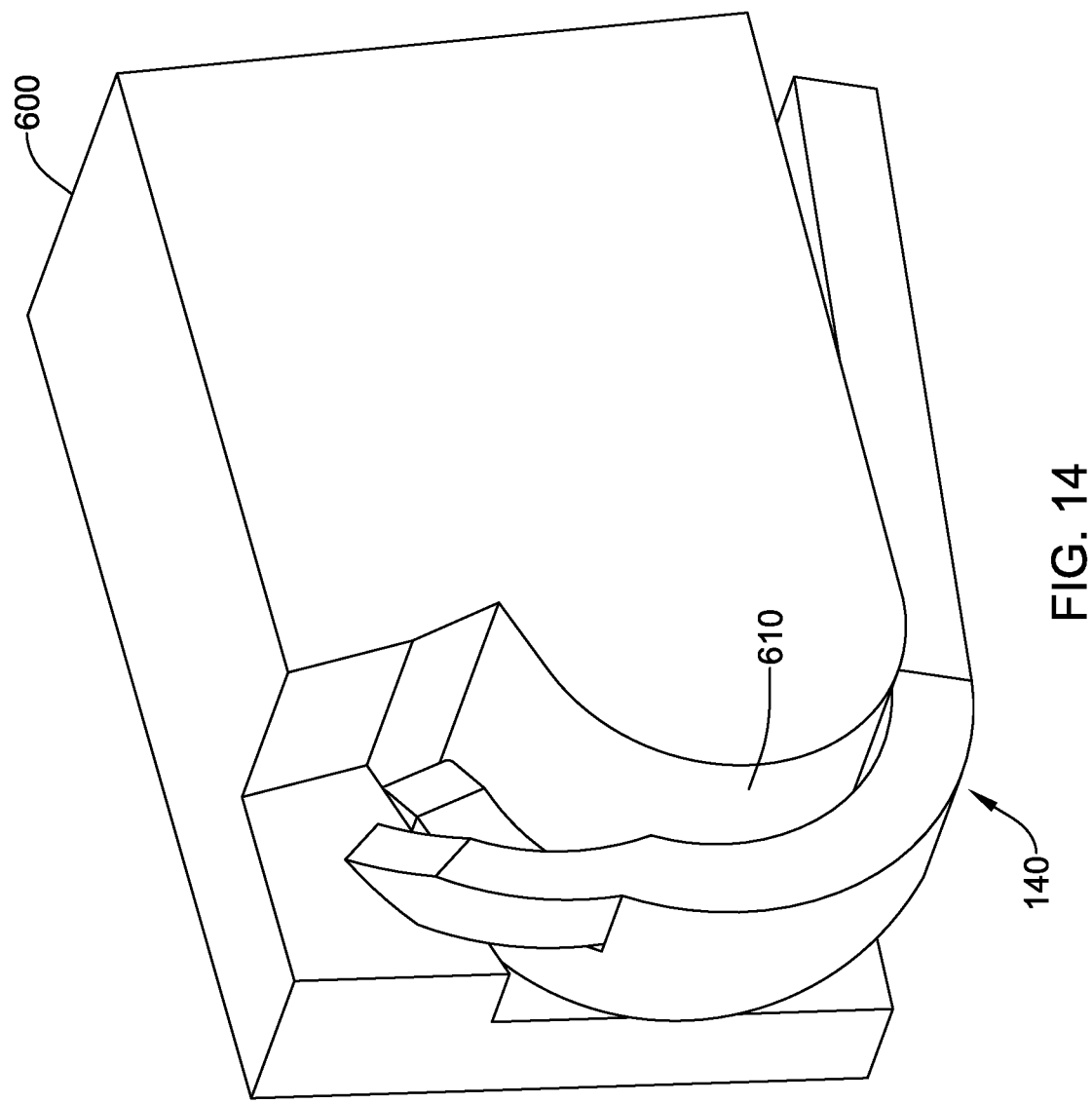
FIG. 14 illustrates selected aspects of shape set tooling associated with the occlusive implant.

In some embodiments, a method of manufacturing the occlusive implant 100 may include cutting the expandable framework 110 from a tubular member, such as a nitinol tube, a metallic tube, etc. as discussed herein. In some embodiments, cutting the expandable framework 110 may include cutting the plurality of anchor members 140 from the tubular member as a monolithic and/or unitary structure with the expandable framework 110. In some embodiments, shape set tooling 600 may be used to form a shape of the plurality of anchor members 140 in the expanded configuration. A portion of the shape set tooling 600 is shown in FIGS. 14-15. The method may include inserting the expandable framework 110 into the shape set tooling 600 such that the plurality of anchor members 140 extends into a recess formed in the shape set tooling 600 that is configured to receive the plurality of anchor members 140 therein. For illustrative purposes, the plurality of anchor members 240 is illustrated. However, it shall be understood that discussion referring to the plurality of anchor members 140 may refer equally and/or interchangeably to the plurality of anchor members 240, 340, 440, 540 herein. The skilled person will recognize and understand minor modification to the shape set tooling 600 may be made to accommodate differences between the described embodiments, configurations, and/or alternatives. Thereafter, the method may include heat setting the plurality of anchor members 140 and/or the expandable framework 110 in the expanded configuration.

As seen in FIG. 14, the shape set tooling 600 may include a curved surface 610 configured to form the at least a portion of the trunk portion that curves radially outward relative to the root portion and/or the first curved surface of the first branch of the plurality of branches. The shape set tooling 600 may be configured to constrain the first branch of the plurality of branches against the curved surface 610 of the shape set tooling 600. In at least some embodiments, the shape set tooling 600 may be configured to leave branches of the plurality of branches other than the first branch unconstrained, thereby allowing those other branches to deflect differently than the first branch, as shown in FIG. 14.

In some embodiments, the plurality of anchor members 140 and/or the plurality of branches may be formed with a curve (e.g., the at least a portion of the trunk portion that curves radially outward relative to the root portion and/or the first curved surface of the first branch of the plurality of branches) prior to inserting into the shape set tooling 600. In such embodiments, the shape set tooling 600 in combination with the heat setting step may be configured to heat set the plurality of anchor members 140 in a desired configuration. For example, the first branch and the second branch may be defined by identical radii (e.g., a common radius length) but different centers after heat setting in the shape set tooling 600. Other configurations are also contemplated.

FIG. 15 illustrates an alternative configuration of the shape set tooling 600 further including a second curved surface 620 configured to form the second curved surface of the second branch of the plurality of branches. In such a configuration, the shape set tooling 600 may be configured to constrain the first branch of the plurality of branches against the curved surface 610 of the shape set tooling 600 and the second branch of the plurality of branches against the second curved surface 620 of the shape set tooling 600. In such a configuration, it may be possible to skip forming one or more curves in the plurality of anchor members 140 and/or the plurality of branches prior to inserting into the shape set tooling 600 and/or prior to the heat setting step. Other configurations are also contemplated.

The materials that can be used for the various components of the system (and/or other elements disclosed herein) and the various components thereof disclosed herein may include those commonly associated with medical devices and/or systems. For simplicity purposes, the following discussion refers to the system. However, this is not intended to limit the devices and methods described herein, as the discussion may be applied to other elements, members, components, or devices disclosed herein, such as, but not limited to, the occlusive implant, the sheath, the core wire, the expandable framework, the occlusive element, the shape set tooling, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable metals and metal alloys include stainless steel, such as 444V, 444L, and 314LV stainless steel; mild steel; nickel-titanium alloy such as linear elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super-elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "super-elastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super-elastic plateau and/or flag region that may be seen with super-elastic nitinol. Thus, for the purposes of this disclosure linear elastic and/or non-superelastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super-elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a super-elastic alloy, for example a super-elastic nitinol can be used to achieve desired properties.

In at least some embodiments, portions or all of the system and/or other elements disclosed herein may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the system and/or other elements disclosed herein. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the system and/or other elements disclosed herein to achieve the same result.

In some embodiments, a degree of Magnetic Resonance Imaging (MRI) compatibility is imparted into the system and/or other elements disclosed herein. For example, the system and/or components or portions thereof may be made of a material that does not substantially distort the image and create substantial artifacts (e.g., gaps in the image). Certain ferromagnetic materials, for example, may not be suitable because they may create artifacts in an MRI image. The system or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the system and/or other elements disclosed herein may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

In some embodiments, the system and/or other elements disclosed herein may include a fabric material disposed over or within the structure. The fabric material may be composed of a biocompatible material, such a polymeric material or biomaterial, adapted to promote tissue ingrowth. In some embodiments, the fabric material may include a bioabsorbable material. Some examples of suitable fabric materials include, but are not limited to, polyethylene glycol (PEG), nylon, polytetrafluoroethylene (PTFE, ePTFE), a polyolefinic material such as a polyethylene, a polypropylene, polyester, polyurethane, and/or blends or combinations thereof.

In some embodiments, the system and/or other elements disclosed herein may include and/or be formed from a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun types. The type and denier of the yarn chosen may be selected in a manner which forms a biocompatible and implantable prosthesis and, more particularly, a vascular structure having desirable properties.

In some embodiments, the system and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); antiproliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps, without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. An occlusive implant system, comprising:
   a sheath including an implant containment area proximate a distal end of the sheath; and
   an occlusive implant comprising an expandable framework configured to shift between a collapsed configuration and an expanded configuration, the expandable framework including a proximal end and a distal end;
   wherein the expandable framework includes a plurality of anchor members extending radially outward from the expandable framework in the expanded configuration, each anchor member including a root portion fixedly attached to the expandable framework and extending distally to a trunk portion in the expanded configuration;
   wherein at least a portion of the trunk portion extends radially outward relative to the root portion in the expanded configuration;
   wherein at least one of the plurality of anchor members includes a plurality of branches extending radially outward from the trunk portion in the expanded configuration;
   wherein recapturing the occlusive implant within the implant containment area after shifting to the expanded configuration includes advancing the distal end of the sheath distally into contact with the plurality of anchor members, wherein contact between the distal end of the sheath and at least one of the plurality of branches urges remaining branches of the plurality of branches away from contact with the sheath.

2. The occlusive implant system of claim 1, wherein each branch contacted by the distal end of the sheath includes a rounded tip and each remaining branch includes a sharpened tip.

3. The occlusive implant system of claim 2, wherein each sharpened tip is disposed distal of each rounded tip as measured parallel to a central longitudinal axis of the expandable framework.

4. The occlusive implant system of claim 1, wherein distal advancement of the sheath after contact between the distal end of the sheath and at least one of the plurality of branches deflects the at least one of the plurality of anchor members at the trunk portion.

5. The occlusive implant system of claim 1, wherein each branch of the plurality of branches has a concave cross-section facing toward the proximal end of the expandable framework in the expanded configuration.

* * * * *